(12) United States Patent
Greenhut et al.

(10) Patent No.: US 9,168,380 B1
(45) Date of Patent: Oct. 27, 2015

(54) SYSTEM AND METHOD FOR TRIGGERED PACING

(71) Applicant: Medtronic, Inc., Minneapolis, MN (US)

(72) Inventors: Saul E Greenhut, Aurora, CO (US); James K Carney, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/340,248

(22) Filed: Jul. 24, 2014

(51) Int. Cl.
*A61N 1/368* (2006.01)
*A61N 1/365* (2006.01)
*A61N 1/362* (2006.01)
*A61N 1/375* (2006.01)
*A61N 1/372* (2006.01)

(52) U.S. Cl.
CPC .............. *A61N 1/365* (2013.01); *A61N 1/3621* (2013.01); *A61N 1/3622* (2013.01); *A61N 1/3756* (2013.01); *A61N 1/37211* (2013.01)

(58) Field of Classification Search
None
See application file for complete search history.

(56) References Cited

U.S. PATENT DOCUMENTS

| | | | |
|---|---|---|---|
| 4,343,311 A | 8/1982 | Markowitz | |
| 5,117,824 A | 6/1992 | Keimel | |
| 5,312,445 A | 5/1994 | Nappholz | |
| 5,331,966 A | 7/1994 | Bennett | |
| 5,354,316 A | 10/1994 | Keimel | |
| 5,545,186 A | 8/1996 | Olson | |
| 5,855,593 A | 1/1999 | Olson | |
| 6,393,316 B1 | 5/2002 | Gillberg | |
| 6,505,067 B1 | 1/2003 | Lee | |
| 6,760,615 B2 | 7/2004 | Ferek-Petric | |
| 6,810,283 B2 | 10/2004 | Suribhotla | |
| 7,027,858 B2 | 4/2006 | Cao | |
| 7,392,085 B2 * | 6/2008 | Warren et al. | 607/27 |
| 7,742,812 B2 | 6/2010 | Ghanem | |
| 7,904,153 B2 | 3/2011 | Greenhut | |
| 8,095,207 B2 | 1/2012 | Belalcazar | |
| 8,160,684 B2 | 4/2012 | Ghanem | |
| 8,160,686 B2 * | 4/2012 | Allavatam et al. | 600/516 |
| 8,352,025 B2 | 1/2013 | Jacobson | |
| 8,433,409 B2 * | 4/2013 | Johnson et al. | 607/36 |
| 8,532,785 B1 | 9/2013 | Crutchfield | |
| 8,538,524 B2 | 9/2013 | Rosenberg | |
| 8,541,131 B2 | 9/2013 | Lund | |
| 8,718,793 B2 * | 5/2014 | O'Connor | 607/119 |
| 8,744,572 B1 | 6/2014 | Greenhut | |
| 2005/0010120 A1 | 1/2005 | Jung | |
| 2006/0116593 A1 | 6/2006 | Zhang | |
| 2012/0172892 A1 | 7/2012 | Grubac | |
| 2012/0303084 A1 | 11/2012 | Kleckner | |
| 2013/0138006 A1 | 5/2013 | Bornzin | |
| 2014/0257421 A1 * | 9/2014 | Sanghera et al. | 607/7 |

FOREIGN PATENT DOCUMENTS

WO 03003905 A2 1/2003

* cited by examiner

*Primary Examiner* — Kennedy Schaetzle
(74) *Attorney, Agent, or Firm* — Evans M. Mburu

(57) ABSTRACT

A medical device system including an intracardiac pacemaker is configured to receive by an implantable medical device sensing module a first cardiac signal using a first pair of electrodes implanted outside the cardiovascular system and identify a P-wave from the first cardiac signal. The system transmits a wireless trigger signal to the intracardiac pacemaker in response to identifying the P-wave. The intracardiac pacemaker delivers a pacing therapy in response to the trigger signal.

21 Claims, 11 Drawing Sheets

SYSTEM AND METHOD FOR TRIGGERED PACING

TECHNICAL FIELD

The disclosure relates to an implantable medical device system and associated method for acquiring electrocardiogram (ECG) signals and delivering therapeutic stimulation pulses using a triggered therapy delivery device.

BACKGROUND

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks.

Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in which one or more heart chambers are electrically paced to restore or improve heart chamber synchrony. Improved heart chamber synchrony is expected to alleviate symptoms of heart failure.

Achieving a positive clinical benefit from CRT, however, may be dependent on several therapy control parameters, such as the timing intervals used to control pacing pulse delivery, e.g. an atrio-ventricular (AV) interval and/or an inter-ventricular (VV) interval. The AV interval controls the timing of ventricular pacing pulses relative to an atrial depolarization. The VV interval controls the timing of a pacing pulse in one ventricle relative to a sensed R-wave in the other ventricle. Pacing may be delivered in the right ventricle (RV) and/or the left ventricle (LV) to restore ventricular synchrony.

Medical device technology advancement has led toward smaller and smaller implantable devices. Recently, leadless intracardiac pacemakers have been introduced which can be implanted directly in a heart chamber. Elimination of transvenous, intracardiac leads has several advantages. For example, complications due to infection associated with a lead extending from a subcutaneous pacemaker pocket transvenously into the heart can be eliminated. Other complications such as "twiddler's syndrome", lead fracture or poor connection of the lead to the pacemaker are eliminated in the use of a leadless, intracardiac pacemaker. New challenges arise, however, in controlling an intracardiac pacemaker to deliver pacing pulses in synchrony with paced or sensed events occurring in other heart chambers, e.g. for delivering effective CRT.

DETAILED DESCRIPTION

An implantable medical device (IMD) system and associated techniques are disclosed herein for sensing cardiac signals (that are indicative of activity of a patient's heart) by a sensing device using electrodes implanted outside the cardiovascular system. As used in this disclosure, the phrase "sensing cardiac signals" is used to refer to the process of acquiring cardiac signals which are indicative of activity of a patient's heart. The cardiac signals may include electrical signals of cardiac depolarization, or mechanical signals of cardiac wall motion, or any other signals that are representative of activity of a patient's heart. As is known in the art, the cardiac signals are processed to generate electrocardiogram (ECG) signals.

The sensing device may be implanted subcutaneously, submuscularly or intrathoracically and is configured to sense cardiac signals for triggering an intracardiac pacemaker to deliver an automatic therapy to the patient's heart based on the timing of the ECG signals. A trigger signal is initiated by the sensing device and detected by a transducer included in the pacemaker. Automatic therapy delivery is achieved by the separate sensing and therapy delivery devices without requiring the two devices to be physically connected to each other.

Among other things, elimination of the physical connection between the sensing and therapy delivery components of an IMD system enables minimally invasive implant procedures to be used, down-sizing of IMD system components and power supply, and/or elimination of some components such as medical leads, sensing capability in the intracardiac pacemaker, and a radio frequency (RF) transmitter in the intracardiac pacemaker.

As used herein, a "trigger signal" is a signal emitted by a transducer when an electrical signal is applied to the transducer. The trigger signal is a command, which is generated by and sent from the sensing device to the intracardiac pacemaker via an emitting device to trigger the delivery of therapy by the pacemaker upon detection of the trigger signal. Examples of a trigger signal include an acoustical signal, e.g. sound waves having a frequency in the ultrasonic range produced by an acoustical transducer, an optical signal produced by a light emitting diode (LED), vertical cavity surface emitting laser (VCSEL) or other optical transducer or an RF signal emitted by an RF antenna.

Figure 1:
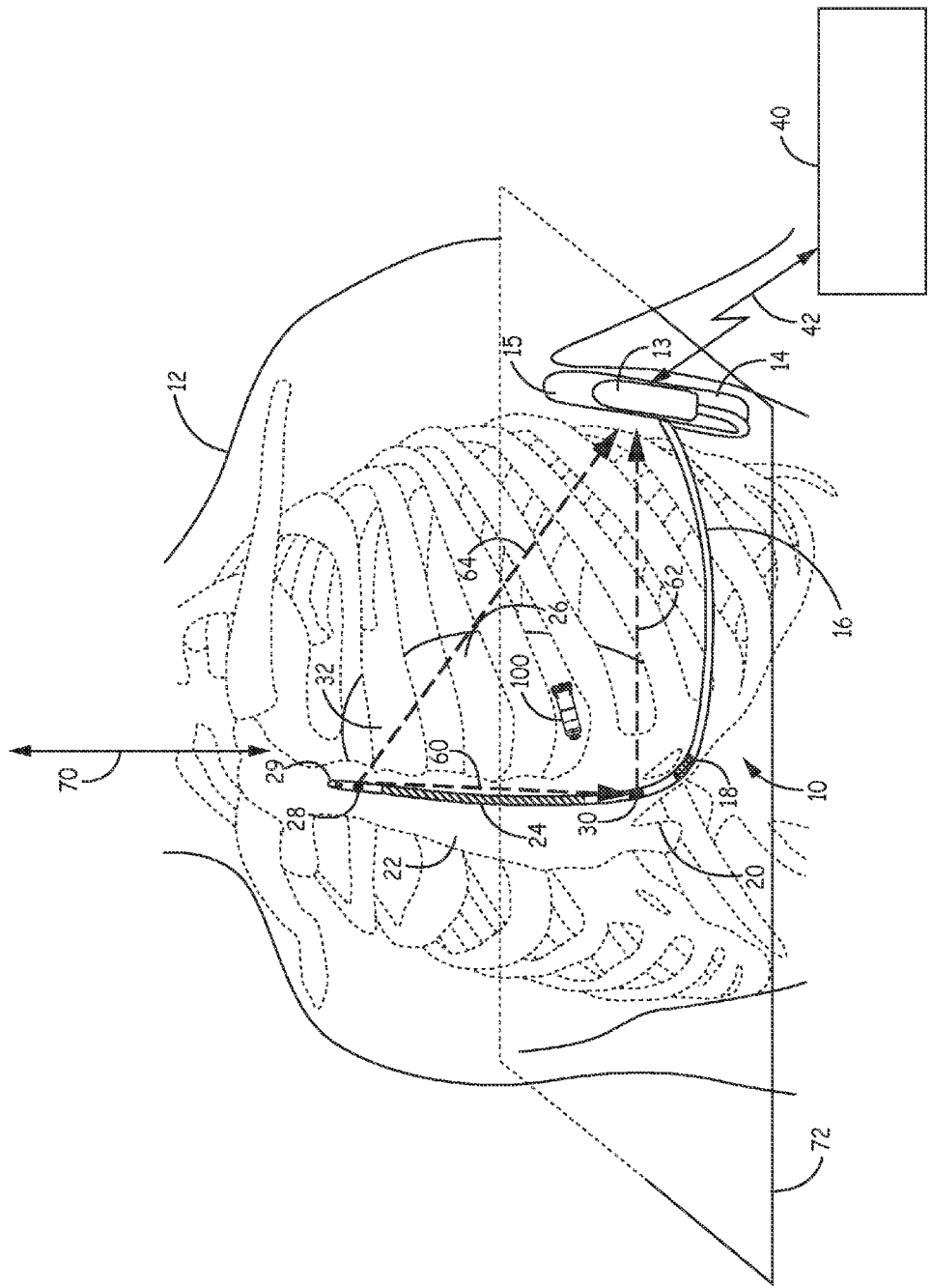
FIG. 1 is a conceptual diagram illustrating an implantable medical device (IMD) system used to sense cardiac electrical signals in a patient and provide therapy to the patient's heart.

FIG. 1 is a conceptual diagram illustrating an IMD system 10 used to sense cardiac electrical signals in patient 12 and provide therapy to heart 26. IMD system 10 includes a therapy delivery device embodied as an intracardiac pacemaker 100 and a sensing device embodied as an ICD 14 coupled to an extravascular lead 16. ICD 14 is implanted subcutaneously on the left side of patient 12. Defibrillation lead 16, which is connected to ICD 14, extends medially from ICD 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is offset laterally to the left side of the body of sternum 22 (i.e., towards the left side of patient 12, offset to the right of sternum 22 or over sternum 22.

Defibrillation lead 16 includes a defibrillation electrode 24, which may be an elongated coil electrode, a pair of sensing electrodes 28 and 30, and trigger signal emitting device 18. Defibrillation lead 16 is placed along sternum 22 such that a therapy vector between defibrillation electrode 24 and a second electrode (such as a portion of the housing 15 of ICD 14 or an electrode placed on a second lead) is substantially across one or both ventricles of heart 26. The therapy vector may, in one example, be viewed as a line that extends from a point on the defibrillation electrode 24 to a point on the housing 15 (or can electrode) of ICD 14. In another example, defibrillation lead 16 may be placed along sternum 22 such that a therapy vector between defibrillation electrode 18 and a housing or can electrode of ICD 14 (or other electrode) is substantially across an atrium of heart 26. In this case, system 10 may be used to provide atrial therapies, such as therapies to treat atrial fibrillation.

Figure 2:
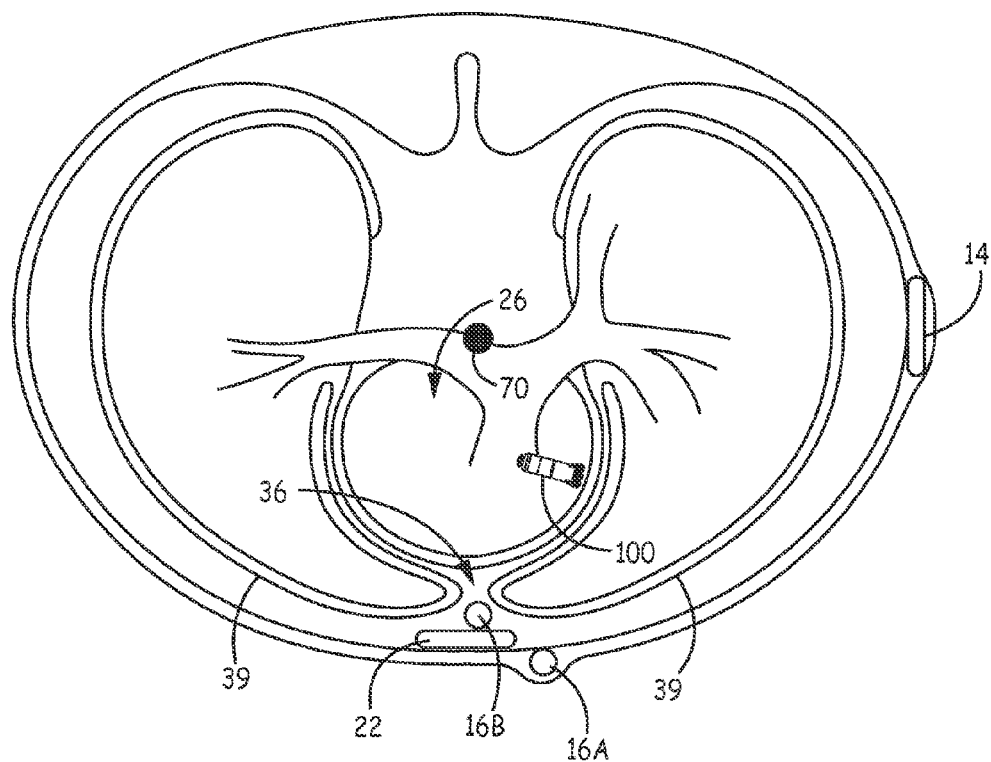
FIG. 2 is a sectional view of a patient depicting an alternative configuration of the IMD system shown in FIG. 1.

Lead 16 is advanced suprasternally remaining external to the thoracic cavity. In other embodiments, as shown in FIG. 2, lead 16 may be advanced substernally or within ribcage 32, i.e. intra-thoracically. Trigger signal emitting device 18 is positioned to establish a signal pathway between emitting device 18 and a receiver included in intracardiac pacemaker 100 that does not excessively attenuate the trigger signal. Trigger signal emitting device 18 may be positioned anywhere along lead 16 such that it is positioned along ribcage 32 or an intercostal space, along the sternum 22, near xyphoid process 20, or other desired location. In other examples, a trigger signal emitting device 18 is carried by a separate lead other than lead 16 or is a leadless device that receives wireless communication signals from ICD 14 that control when trigger signal emitting device 18 sends a trigger signal to pacemaker 100. In still other examples, emitting device 18 is incorporated in ICD 14, e.g. in or along ICD housing 14 or connector block 13.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 may follow a different path, e.g., across the upper chest area and inferior along sternum 22. When the ICD 14 is implanted in the pectoral region, the system 10 may include a second lead including a defibrillation electrode that extends along the left side of the patient such that the defibrillation electrode of the second lead is located along the left side of the patient to function as an anode or cathode of the therapy vector for defibrillating heart 26.

ICD 14 includes a housing 15 that forms a hermetic seal that protects components within ICD 14. The housing 15 of ICD 14 may be formed of a conductive material, such as titanium or other biocompatible conductive material or a combination of conductive and non-conductive materials. Housing 15 may enclose one or more components, including processors, memories, transmitters, receivers, sensors, sensing circuitry, therapy circuitry and other appropriate components (often referred to herein as modules). In some instances, the housing 15 functions as an electrode (sometimes referred to as a housing electrode or can electrode) that is used in combination with one of electrodes 24, 28 and 30 to deliver a therapy to heart 26 or to sense electrical activity of heart 26.

ICD 14 may also include a connector assembly 13 (also referred to as a connector block or header) for receiving a proximal connector (not illustrated) of lead 16. Connector assembly 13 includes electrical feedthroughs through which electrical connections are made between conductors within defibrillation lead 16 and electronic components included within the housing. Depending on the intended implant location of ICD 14, a trigger signal emitting device may be included in connector assembly 13 in addition to or in place of the emitting device 18 carried by lead 16 for transmitting trigger signals to pacemaker 100.

Defibrillation lead 16 includes a lead body having a proximal end that includes a connector configured to connect to ICD 14 (via connector assembly 13) and a distal end that includes one or more electrodes 24, 28 and 30 and trigger signal emitting device 18. The lead body of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions. Although defibrillation lead 16 is illustrated as including three electrodes 24, 28 and 30, defibrillation lead 16 may include more or fewer electrodes. For example, if pacemaker 100 is implemented with a sensing device that is not enabled to deliver cardioversion and defibrillation therapies, defibrillation electrode 24 may not be present. Two or more sensing electrodes may be included for sensing an extracardiac cardiac signal.

Defibrillation lead 16 includes elongated electrical conductors (not illustrated) that extend within the elongated lead body from the connector on the proximal end of defibrillation lead 16 to the respective electrodes 24, 28 and 30 and emitting device 18. In other words, each of the elongated electrical conductors contained within the lead body of defibrillation lead 16 may engage with respective ones of electrodes 24, 28 and 30 and emitting device 18. When the connector at the proximal end of defibrillation lead 16 is connected to connector assembly 13, the respective conductors electrically couple to circuitry of ICD 14, such as a therapy module, a sensing module, or trigger signal drive circuit, via connections in connector assembly 13, including associated feedthroughs. The electrical conductors transmit electrical stimulation pulses from a therapy module within ICD 14 to one or more of electrodes 24, 28 and 30 and transmit sensed electrical signals from one or more of electrodes 24, 28 and 30 to the sensing module within ICD 14.

Electrical conductors extending from the proximal lead connector to emitting device 18 conduct an electrical control signal to emitting device 18 to cause emitting device 18 to emit a trigger signal at appropriate times for causing intracardiac pacemaker 100 to deliver one or more pacing pulses to heart 26.

A "triggered pacemaker" as used herein is a device that is triggered by the trigger signal to deliver a therapy to the patient's heart or another targeted patient tissue. In the illustrative embodiments described herein, the intracardiac pacemaker delivers an electrical stimulation therapy, such as cardiac pacing pulses. The triggered pacemaker includes a transducer that produces an electrical signal in response to being subjected to the trigger signal. The electrical signal is compared to a trigger signal detection threshold and causes the therapy delivery device to deliver a therapeutic stimulation pulse to a targeted tissue of the patient when the detection threshold is exceeded. The "triggered pacemaker" as disclosed herein, therefore, is, at least some of the time, not making a decision to deliver therapy based on sensing and processing of a physiological signal sensed using a transducer such as a pressure transducer, optical transducer, electrode or other transducer to produce a time-varying signal waveform (e.g. ECG, blood pressure, etc.) correlated to a physiological condition or physiological events. The decision to deliver therapy is made by a sensing device, in this case ICD 14, that is controlling the emitting device 18 that emits the trigger signal. The ICD 14 and the pacemaker 100 need not be in wired connection with each other.

ICD 14 may sense electrical activity of heart 26 via one or more sensing vectors that include combinations of electrodes 28 and 30 and a housing 15 or can electrode of ICD 14. For example, ICD 14 may obtain electrical signals sensed using a sensing vector between electrodes 28 and 30, between electrode 28 and the conductive housing 15, between electrode 30 and the conductive housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15 of ICD 14.

In one example, a cardiac signal is acquired by ICD 14 along a cranial-caudal vector 60 defined by electrodes 28 and 30 that extends approximately parallel to a cranial-caudal axis 70 of the patient 12 and approximately normal to a transverse plane 72 of patient 12. The cardiac signal is processed to generate an ECG signal. As used herein, the term "approximately parallel to" with reference to an anatomical axis refers to being within an angle of 30 degrees of the named axis. As used herein the term "approximately normal to" with reference to an anatomical axis or anatomical plane refers to being more than an angle of 60 degrees from the named axis or plane. As such, in one example cranial-caudal vector 60 extends at an angle that is less than 30 degrees from axis 70 and more than 60 degrees angle from transverse plane 72. Cranial-caudal vector 60 may be along or near a median sagittal plane of patient 12 or laterally offset from the median sagittal plane of patient 12. An ECG sensing vector that is generally directed cranially or caudally, approximately parallel to cranial-caudal axis 70 and approximately normal to a transverse plane 72 is referred to herein as a "cranial-caudal vector" or simply as a "cranial vector" or "cranial ECG vector".

As described below, a cranial ECG vector is used to identify cardiac events for use in controlling the emitting device 18 to send trigger signals to pacemaker 100. A "cardiac event" as used herein refers to a cardiac signal attendant to a depolarization or repolarization of the myocardium. Accordingly, cardiac events may include P-waves occurring with atrial depolarization, R-waves occurring with ventricular depolarization, and T-waves occurring with ventricular repolarization. In some embodiments, a cranial ECG vector is used to identify P-waves for controlling emitting device 18 to send trigger signals to pacemaker 100 in timed relation to P-waves to cause pacemaker 100 to deliver a ventricular pacing pulse at a desired AV interval.

As indicated above, defibrillation lead 16 may be implanted in other positions than the general position shown in FIG. 1. For example, lead 16 may be further inferior or superior or shifted laterally. Lead 16 carrying a pair of sensing electrodes 28 and 30, however, is positioned in a substantially vertical configuration (when the patient is in an upright position) in some examples such that electrodes 28 and 30 define an ECG sensing vector that is approximately parallel to the cranial-caudal axis 70 of the patient. As described below, a cranial ECG vector may be relatively more sensitive to P-waves than non-cranial ECG sensing vectors and may therefore be used to sense P-waves for use in controlling therapy delivery by triggered pacemaker 100. In other examples, however, when lead 16 is not positioned in the substantially vertical configuration as shown, for example extending relatively more diagonally or horizontally, a pair of the available electrodes 24, 28, 30 and housing electrode 15 that is most closely aligned with a cranial-caudal axis 70 of the patient than any of the other available pairs of electrodes may be selected for sensing and identifying P-waves for use in controlling triggered pacemaker 100.

In one example, electrode 28 is superior to the fourth intercostal space that generally corresponds to the cranial-caudal location of surface ECG V1 and V2 electrodes. Electrode 30 is inferior to electrode 28 along cranial-caudal vector 60. For example, electrode 30 may be cranial to the seventh intercostal space but inferior to electrode 28. In another example, electrode 30 is positioned along the xyphoid process 20. The electrode spacing between electrodes 28 and 30 may vary between embodiments. For example, without any limitation intended, electrodes 28 and 30 may be spaced apart approximately 1 inch to approximately 6 inches along lead 16. In one example, the spacing between electrodes 28 and 30 is more than 1.5 inches. In another example, the spacing between electrodes 28 and 30 is more than 2 inches. In yet another example, the spacing is at least five inches. As used herein, the term "approximately" with reference to a numerical value is within 10% of the stated value in some examples.

FIG. 2 is a sectional view of patient 12 depicting an alternative configuration of system 10. In the example illustrated in FIG. 1, lead 16 is implanted subcutaneously, e.g., between the skin and the ribs or sternum. In other instances, lead 16 may be implanted at other extravascular locations. As shown in FIG. 2, lead 16 may be implanted at least partially in a substernal location. In such a configuration, a portion 16A of lead 16 extends subcutaneously from ICD 14 toward sternum 22 and at least a portion 16B of lead 16 is advanced under or below the sternum in the mediastinum 36 and, more particularly, in the anterior mediastinum. The anterior mediastinum is bounded laterally by pleurae 39, posteriorly by pericardium, and anteriorly by sternum 22. Lead 16 may be at least partially implanted in other intrathoracic locations, e.g., locations in the region around, but not in direct contact with, the outer surface of heart 26. These other intrathoracic locations may include in the mediastinum 36 but offset from sternum 22, in the superior mediastinum, in the middle mediastinum, in the posterior mediastinum, in the sub-xiphoid or inferior xiphoid area, near the apex of the heart, or other location not in direct contact with heart 26 and not subcutaneous. In FIG. 2, the substernal portion 16B of lead 16 is positioned approximately parallel to cranial-caudal axis 70 to enable sensing of P-waves from a cardiac signal obtained from a cranial ECG vector. Other intrathoracic locations of lead 16 may be used in other examples that still enable sensing of P-waves along a cranial ECG vector.

Referring again to FIG. 1, additional ECG vectors 62 and 64 may be sensed between electrode 30 and housing electrode 15 and/or between electrode 28 and housing electrode 15, respectively. An ECG vector, such as vector 62 or 64, that is acquired along a vector that extends at an angle greater than 30 degrees from cranial-caudal axis 70 is referred to herein as a "non-cranial vector" or "non-cranial ECG vector." In some examples, a non-cranial vector is a vector extending at an angle that is equal to or less than 60 degrees from a transverse plane 72 of the patient's body. The ECG vector 62 between electrode 30 and housing electrode 15 is referred to herein as a "lateral vector" or "lateral ECG vector" because it extends laterally approximately in a transverse plane 72, (within 30 degrees of the transverse plane 72) and approximately normal to cranial-caudal axis 70. The ECG vector 64 between electrode 28 and housing electrode 15 is referred to herein as a "diagonal vector" or "diagonal ECG vector" since it extends diagonally to both cranial-caudal axis 70 and transverse plane 72, e.g. at an angle that is between 30 and 60 degrees from cranial-caudal axis 70.

Figure 6:
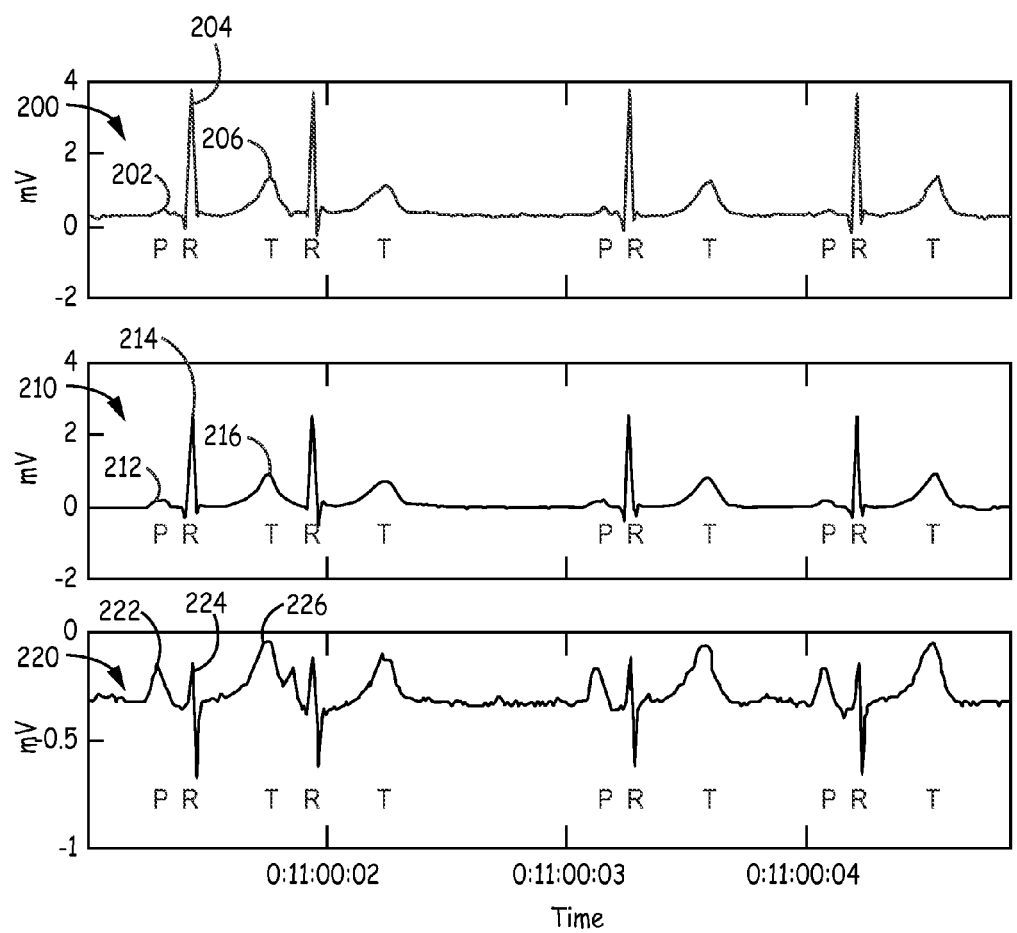
FIG. 6 depicts electrocardiograms recorded using subcutaneous (or substernal) electrodes implanted outside the cardiovascular system.

As described in conjunction with FIG. 6, lateral ECG sensing vector 62 and diagonal ECG sensing vector 64 are relatively less sensitive to P-waves than cranial vector 60. These non-cranial vectors 62 and 64 have high signal-to-noise ratios for sensing R-waves however. As such, a cardiac signal acquired from lateral vector 62 and/or diagonal vector 64 is/are used to eliminate or reject R-waves and T-waves from the ECG acquired from cranial vector 60 to aid in identifying P-wave signals from the cranial ECG vector 60.

ICD 14 also analyzes the sensed cardiac signal to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 24 of defibrillation lead 16 and the housing 15. Cardiac event signals sensed from the lateral vector 62 and/or diagonal vector 64 may be used alone or in combination with signals sensed from cranial vector 60 for detecting tachyarrhythmias in a variety of detection algorithms.

Electrodes 28 and 30 may comprise ring electrodes, hemispherical electrodes, coil electrodes, helix electrodes, segmented electrodes, directional electrodes, or other types of electrodes, or combination thereof. Electrodes 28 and 30 may be the same type of electrodes or different types of electrodes, although in the example of FIG. 1 both electrodes 28 and 30 are illustrated as ring electrodes. Electrodes 28 and 30 may be used for sensing cardiac signals that include P-waves and R-waves for use in controlling the timing of an R-wave synchronized shock or controlling timing of pacing pulses delivered by pacemaker 100. In some instances, one or more pacing therapies may be delivered prior to or after delivery of a defibrillation shock by ICD 14, such as anti-tachycardia pacing (ATP) or post shock pacing. In these instances, ICD 14 may generate and deliver pacing pulses via therapy vectors that include one or both of electrodes 28 and 30 and/or the housing 15. Alternatively, ICD 14 causes trigger signal emitting device 18 to emit trigger signals to cause pacemaker 100 to deliver pacing pulses to heart 26 at appropriate times.

Defibrillation lead 16 may also include an attachment feature 29 at or toward the distal end of lead 16. The attachment feature 29 may be a loop, link, or other attachment feature. For example, attachment feature 29 may be a loop formed by a suture. As another example, attachment feature 29 may be a loop, link, ring of metal, coated metal or a polymer. The attachment feature 29 may be formed into any of a number of shapes with uniform or varying thickness and varying dimensions. Attachment feature 29 may be integral to the lead or may be added by the user prior to implantation. Attachment feature 29 may be useful to aid in implantation of lead 16 and/or for securing lead 16 to a desired implant location.

In some instances, defibrillation lead 16 may include a fixation mechanism in addition to or instead of the attachment feature. For example, defibrillation lead 16 may also include a suture sleeve or other fixation mechanism (not shown) located proximal to electrode 30 or near emitting device 18 that is configured to fixate lead 16 near the xiphoid process or lower sternum location. The fixation mechanism (e.g., suture sleeve or other mechanism) may be integral to the lead or may be added by the user prior to implantation. For example, a fixation mechanism may be used to stably locate emitting device 18 inferior to the xyphoid process 20 or along an intercostal space to prevent rotation or shifting of the emitting device 18 that may cause signal misdirection or signal loss due to interference by body tissues. Attachment feature 29 and/or a more proximal fixation mechanism may be used to anchor lead 16 to maintain a desired cranial vector between electrodes for sensing P-waves.

Lead 16 includes a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly 13 of ICD 14. In some instances, lead 16 may include an attachment feature at the proximal end of lead 16 that may be coupled to an implant tool to aid in implantation of lead 16. The attachment feature at the proximal end of the lead may separate from the connector and may be either integral to the lead or added by the user prior to implantation.

ICD 14 is illustrative in nature and should not be considered limiting of the type of sensing device and associated techniques described in this disclosure. For instance, ICD 14 may include shock therapy capabilities in addition to sensing cardiac signals without pacing therapy capabilities. In other examples, ICD 14 may be coupled to more than one lead for sensing cardiac signals and/or sending trigger signals to pacemaker 100. In other examples, a sensing device that receives cardiac signals for identifying P-waves may not include therapy delivery capabilities.

Pacemaker 100 is a transcatheter intracardiac pacemaker adapted for implantation wholly within a heart chamber, e.g. wholly within the RV, wholly within the LV, wholly within the right atrium (RA) or wholly within the left atrium (LA) of heart 26. In the examples of FIGS. 1 and 2, pacemaker 100 is positioned proximate to an inner wall of the LV to provide left ventricular pacing. In other examples, pacemaker 100 is positioned proximate to an inner wall of the right ventricle to provide right ventricular pacing. In other examples, pacemaker 100 may be positioned at any other location outside or within heart 26, including epicardial locations. For example, pacemaker 100 may be positioned outside or within the right atrium or left atrium, e.g., to provide respective right atrial or left atrial pacing. In other embodiments, pacemaker 100 may be embodied as therapy delivery device for delivering an electrical stimulation therapy at another body location. Depending on the implant location, pacemaker 100 may be configured to deliver an electrical stimulation therapy to target therapy site(s) other than the myocardium. For example, pacemaker 100 may provide atrioventricular nodal stimulation, fat pad stimulation, vagal stimulation, or other types of neurostimulation.

Pacemaker 100 is capable of producing electrical stimulation pulses delivered to heart 26 via one or more electrodes on the outer housing of pacemaker 100.

Pacemaker 100 includes a receiving transducer for receiving a trigger signal emitted by emitting device 18. In response to detecting the trigger signal, pacemaker 100 delivers one or more pacing pulses.

While FIG. 1 shows one pacemaker 100 positioned in one heart chamber (the LV), it is contemplated that a second, triggered intracardiac pacemaker is positioned in the right ventricle (RV) in some examples. Both the LV pacemaker 100 and the second RV intracardiac pacemaker may receive a trigger signal emitted by emitting device 18 to coordinate biventricular pacing in response to P-waves sensed by ICD 14 according to the techniques disclosed herein.

In one embodiment, pacemaker 100 includes a pulse generator configured to deliver one or more pacing pulses upon receiving the trigger signal from emitting device 18. Pacemaker 100 may not be configured to sense cardiac signals. Cardiac signal sensing is performed by ICD 14. ICD 14 senses cardiac signals through lead 16 and controls pacing delivered by pacemaker 100 via trigger signals emitted by emitting device 18 under the control of ICD 14.

An intracardiac pacemaker 100 may not be configured to sense cardiac signals. As a result, the ability to independently deliver CRT, anti-tachycardia pacing (ATP) or post shock pacing, or other types of pacing therapies that are synchronized with paced or sensed events occurring in another cardiac chamber may be limited. In order to minimize the size of a pacemaker 100, cardiac signal sensing and radio frequency telemetry functions may be omitted such that pacemaker 100 includes a pulse generator with limited memory, processing, and other functions.

In other embodiments, pacemaker 100 senses cardiac electrogram (EGM) signals in the heart chamber in which it is implanted. Since pacemaker 100 is positioned wholly within a heart chamber, the EGM signal sensed by pacemaker 100 will be less sensitive or insensitive to P-waves and/or R-waves occurring in other heart chambers. In past practice, a pacemaker may be coupled to one or more leads that position sense electrodes in or along multiple heart chambers such that multiple sensing channels can be monitored. By monitoring multiple sensing channels, coordinated pacing pulses can be delivered to one or more heart chambers at specified time intervals relative to sensed events in other heart chambers, e.g., AV or VV intervals programmed into the pacemaker.

Since pacemaker 100 may have no or limited sensing capabilities, pacemaker 100 may be "blinded" to events occurring in other heart chambers, such as the atria. Delivery of CRT, dual chamber pacing, or other multi-chamber pacing therapies may require delivering a pacing pulse at a predetermined time interval after an event, sensed or paced, in another heart chamber. As such, emitting device 18 provides a trigger signal to pacemaker 100 in response to cardiac signals sensed by ICD 14 to cause pacing pulses to be delivered by pacemaker 100 at desired time intervals relative to other heart chamber events. Pacemaker 100 (for generating pacing pulses) combined with ICD 14 (for sensing physiological signals and making therapy delivery decisions in response thereto) provides the functionality required to deliver various therapies that may require synchronization or coordination between multiple anatomical sites without physical connection between pacemaker 100 and ICD 14 implanted at separate sites.

FIG. 1 further depicts programmer 40 in wireless communication with ICD 14 via communication link 42. In some examples, programmer 40 comprises a handheld computing device, computer workstation, or networked computing device.

Programmer 40 includes a user interface that presents information to and receives input from a user. It should be noted that the user may also interact with programmer 40 remotely via a networked computing device.

A user, such as a physician, technician, surgeon, electrophysiologist, other caregiver, or patient, interacts with programmer 40 to communicate with ICD 14. For example, the user may interact with programmer 40 to retrieve physiological or diagnostic information from ICD 14. A user may also interact with programmer 40 to program ICD 14, e.g., select values for operational parameters of the ICD 14, including parameters used to control trigger signal emitting device 18 for controlling pacemaker 100. A user may use programmer 40 to retrieve information from ICD 14 regarding the rhythm of heart 26, trends therein over time, or arrhythmic episodes.

As indicated, ICD 14 and programmer 40 communicate via wireless communication. Examples of communication techniques may include low frequency or radiofrequency (RF) telemetry, but other techniques may be used. In some examples, programmer 40 may include a programming head that is placed proximate to the patient's body near the ICD 14 implant site in order to improve the quality or security of communication between ICD 14 and programmer 40.

The system illustrated in FIG. 1 is an example configuration of an IMD system and should not be considered limiting of the techniques described herein. Other arrangements of a sensing device coupled to sensing electrodes for sensing cardiac signals, a trigger signal emitting device, and a triggered pacemaker for detecting the trigger signal and delivering a therapy in response thereto may be conceived. Such systems may implement the techniques disclosed herein for identifying P-waves for use in controlling the trigger signal emitting device to cause the pacemaker to deliver therapy without requiring physical connection between the pacemaker and the sensing device.

Figure 3:
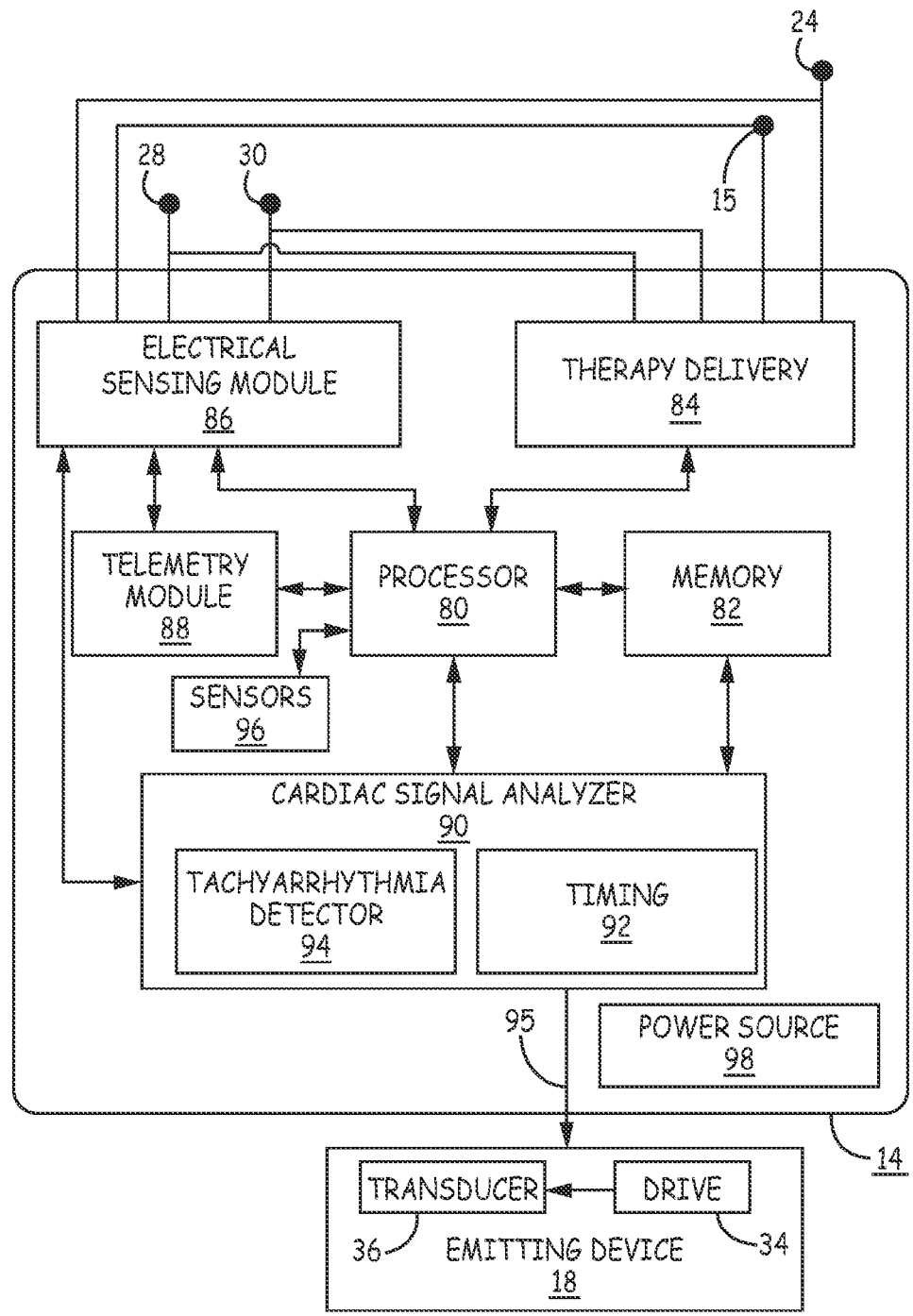
FIG. 3 is a functional block diagram of electronic circuitry that is included in one embodiment of the ICD included in the IMD system of FIG. 1.

FIG. 3 is a functional block diagram of electronic circuitry that is included in one embodiment of ICD 14 shown in FIG. 1. ICD 14 includes processing and control module 80, also referred to herein as "processor" 80, associated memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause processor 80 or other ICD modules to perform various functions attributed to ICD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 and/or pacemaker 100 may be implemented in processing and control module 80 executing instructions stored in memory 82.

Processing and control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16, e.g. as shown in FIG. 1 and housing 15, at least a portion of which also serves as a common or ground electrode and is therefore also referred to herein as "housing electrode" 15.

Electrical sensing module 86 is coupled to electrodes 28 and 30 in order to monitor electrical activity of the patient's heart. Electrical sensing module 86 may additionally be coupled to electrodes 24 and 15 and enabled to selectively monitor one or more sensing vectors selected from the available electrodes 24, 28, 30 and 15. For example, sensing module 86 may include switching circuitry for selecting which of electrodes 24, 28, 30 and housing electrode 15 are coupled to sense amplifiers included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, and housing electrode 15. For example, a sensing vector between electrodes 28 and 30 may be selected for sensing a cranial ECG vector on one channel and at least one additional non-cranial sensing vector is selected between one of electrodes 24, 28 and 30 paired with the housing electrode 15 and sensed on another sensing channel. Each sensing channel may be configured to filter the cardiac signal to improve the signal quality of the desired cardiac event. For example, a cranial vector sensing channel may be configured with a bandpass filter that improves P-wave signal quality. A non-cranial vector sensing channel may be configured with a bandpass filter that improves R-wave signal quality. The non-cranial vector sensing channel may have a higher frequency pass band than the cranial vector sensing channel in some examples.

Sensing module 86 includes one or more sense amplifiers for acquiring the cardiac signals developed across selected electrodes. The sense amplifiers pass sense event signals to cardiac signal analyzer 90. For example sense event signals are passed to cardiac signal analyzer 90 when the sensed cardiac signal crosses a respective sensing threshold, which may be an auto-adjusting sensing threshold.

Processor 80 or cardiac signal analyzer 90 may receive one or more analog or digitized cardiac signals from sensing module 86 that have been sensed using extravascular, extracardiac electrodes. One or more sensing vectors are selected from electrodes 24, 28, 30 and 15 for identifying P-waves. P-waves are identified from ECG signal analysis that enables separation or isolation of P-waves from R-waves and T-waves. In one example, a P-wave sensing threshold is applied to an ECG vector having a highest amplitude P-wave signal compared to other ECG vectors. P-wave sense signals are passed from sensing module 86 to processor 80 in response to P-wave sensing threshold crossings. A second sensing threshold is applied to at least one other ECG vector having relatively lower amplitude P-wave signals that fall below the second sensing threshold. Sensed event signals from the additional ECG vector are also passed to processor 80. Processor 80 identifies P-wave sense signals that are sensed simultaneously with sense event signals from the at least one additional ECG vector. These P-wave sense signals are rejected as being oversensed R-waves or T-waves. Valid P-waves are identified from the first ECG by rejecting P-wave sense event signals that are sensed simultaneously with events from the additional ECG vector.

Timing circuit 92 passes a control signal 95 in response to a valid P-wave sense event signal to control the emitting device 18 to send a trigger signal to pacemaker 100. In this way, pacemaker 100 is controlled by the trigger signal to pace the LV at a desired AV interval. Control of the intracardiac pacemaker 100 is achieved using extracardiac cardiac signals sensed by a separate sensing device, i.e. ICD 14, which identifies P-waves from a selected ECG vector by rejecting non-P-wave events sensed from a second ECG vector.

In some examples, bradycardia or asystole is determined by a pacing escape interval timer expiring within the timing circuit 92. In response to the pacing escape interval expiring, a control signal 95 is passed to the trigger signal emitting device 18. The pacing escape interval is restarted upon a trigger signal or a sense signal.

The control signal 95 in the illustrative examples presented herein may be referred to as a pacing control signal because it causes pacemaker 100 to deliver a pacing pulse to a heart chamber. In other examples, the control signal 95 may be produced by cardiac signal analyzer 90 to cause other types of therapy pulses to be delivered by pacemaker 100 (or another therapy delivery device). For example control signal 95 may be produced to cause pacemaker 100 or another therapy delivery device to deliver an ATP pulse, a vagal nerve stimulation pulse, or other type of electrical stimulation pulse.

The control signal 95 is an electrical signal that is passed to emitting device 18 along lead 16 (or another lead carrying emitting device 18) when emitting device 18 is coupled to ICD 14 in a wired connection. The control signal 95 is alternatively a wireless telemetry signal that is transmitted via telemetry module 88, to emitting device 18. Emitting device 18 may be carried by a lead but configured to wirelessly receive a control signal 95 from telemetry module 88. Alternatively, the emitting device is not a lead-based emitting device and receives control signal 95, e.g. an RF signal, from telemetry module 88.

Trigger signal emitting device 18 includes a drive signal circuit 34 that receives the control signal 95, either as a wired electrical signal or a wireless signal from telemetry module 88. It is understood that in some embodiments, drive signal circuit 34 may be included within the housing 15 of ICD 14 and coupled to transducer 36 located external to housing 15.

Drive signal circuit 34 passes an electrical signal to transducer 36 to enable transducer 36 to emit the trigger signal. Transducer 36 may be an optical transducer or an acoustical transducer in various examples. In other examples, the drive signal circuit 34 is coupled to an antenna for transmitting the trigger signal as an RF signal. The trigger signal is received and detected by pacemaker 100 causing pacemaker 100 to deliver one or more pacing pulses to the patient's heart.

Timing circuit 92 may generate control signal 95 to provide bradycardia pacing, anti-tachycardia pacing, cardiac resynchronization therapy, AV nodal stimulation, or other pacing therapies according to pacing algorithms and timing intervals stored in memory 82. Bradycardia pacing may be delivered temporarily to maintain cardiac output after delivery of a cardioversion-defibrillation shock by ICD 14 as the heart recovers back to normal function post-shock.

Cardiac signal analyzer 90 includes a tachyarrhythmia detector 94 for detecting and discriminating supraventricular tachycardia (SVT), ventricular tachycardia (VT) and ventricular fibrillation (VF). Some aspects of sensing and processing subcutaneous sensed cardiac signals are generally disclosed in commonly-assigned U.S. Pat. No. 7,904,153 (Greenhut, et al.), hereby incorporated herein by reference in its entirety. The timing of R-wave sense signals from sensing module 86 is used by tachyarrhythmia detector 94 to measure R-R intervals for counting RR intervals in different detection zones or determining a heart rate or other rate-based measurements for detecting ventricular tachyarrhythmia. Electrical sensing module 86 may additionally or alternatively provide digitized signals based on the sensed cardiac signal to cardiac signal analyzer 90 for use in detecting tachyarrhythmia. Examples of ICDs that may be adapted for use with a triggered pacemaker 100 and operations that may be performed by tachyarrhythmia detector 94 for detecting, discriminating and treating tachyarrhythmia are generally disclosed in U.S. Pat. No. 7,742,812 (Ghanem, et al.), U.S. Pat. No. 8,160,684 (Ghanem, et al.), U.S. Pat. No. 5,354,316 (Keimel); U.S. Pat. No. 6,393,316 (Gillberg et al.), U.S. Pat. No. 5,545,186 (Olson, et al.), and U.S. Pat. No. 5,855,593 (Olson, et al.), all of which patents are incorporated herein by reference in their entirety.

The detection algorithms are highly sensitive and specific for the presence or absence of life threatening VT and VF. Therapy delivery module 84 includes a high voltage (HV) therapy delivery module including one or more HV output capacitors. When a malignant tachycardia is detected the HV capacitors are charged to a pre-programmed voltage level by a HV charging circuit. Processor 80 applies a signal to trigger discharge of the HV capacitors upon detecting a feedback signal from therapy delivery module 84 that the HV capacitors have reached the voltage required to deliver a programmed shock energy. In this way, processor 80 controls operation of the high voltage output circuit of therapy delivery module 84 to deliver high energy cardioversion/defibrillation shocks using defibrillation electrode 24 and housing electrode 15.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy. Sensors 96 may also be used in determining the need and timing for pacing by pacemaker 100. For example, an activity sensor signal or other rate responsive signal, such as a minute ventilation signal, may be used for determining a pacing rate meeting a patient's metabolic demand. Timing circuit 92 produces a control signal 95 to cause emitting device 18 to generate trigger signals that cause pacemaker 100 to deliver pacing pulses at an appropriate rate based on the rate responsive signal. Sensors 96 may include one or more sensors carried by a lead extending from ICD 14, within or along housing 15, and/or connector block 13.

Telemetry module 88 includes a transceiver and antenna for communicating with another device, such as an external programmer 40 and emitting device 18 when it is configured to receive wireless control signals 95. Under the control of processor 80, telemetry module 88 may receive downlink telemetry from and send uplink telemetry to programmer 40 or other external device. Telemetry module 88 may transmit a control signal wirelessly to emitting device 18, e.g. as an RF signal.

Figure 4:
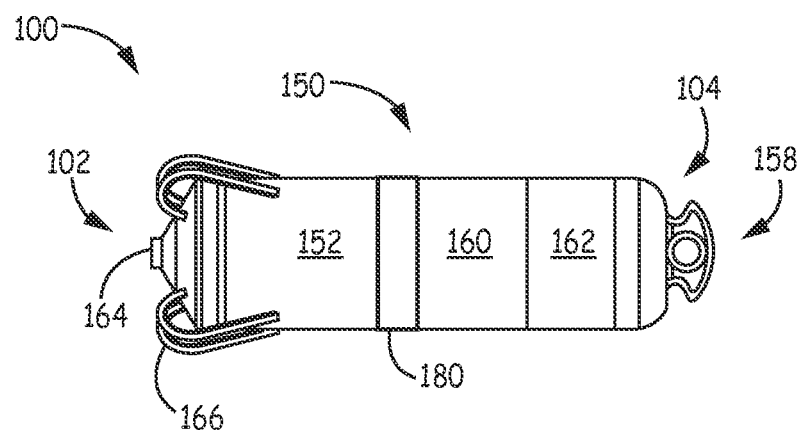
FIG. 4 is a conceptual diagram of an intracardiac pacemaker that may be included in the IMD system of FIG. 1.

FIG. 4 is a conceptual diagram of pacemaker 100. Pacemaker 100 includes electrodes 162 and 164 spaced apart along the housing 150 of pacemaker 100. Electrode 164 is shown as a tip electrode extending from a distal end 102 of pacemaker 100, and electrode 162 is shown as a ring electrode along a mid-portion of housing 150, for example adjacent proximal end 104. In alternative embodiments, pacemaker 100 may include two or more ring electrodes or other types of electrodes exposed along pacemaker housing 150 for delivering electrical stimulation to heart 26. Electrodes 162 and 164 and other electrodes described herein may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

The housing 150 includes a control electronics subassembly 152, which houses the electronics for producing stimulation pulses and performing therapy delivery functions of pacemaker 100. As one example, control electronics subassembly 152 may include a pulse generator and a receiving transducer for receiving the trigger signal from emitting device 18 and triggering the pulse generator to deliver a pacing pulse via electrodes 162 and 164 in response to the trigger signal. In some embodiments, electrodes 162 and 164 are also used for sensing cardiac EGM signals, in which case control electronics subassembly 152 includes sensing circuitry.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150. Electrodes 162 and 164 form an anode and cathode pair for bipolar cardiac pacing.

Pacemaker 100 may include a set of active fixation tines 166 to secure pacemaker 100 to patient tissue, e.g. by interacting with the ventricular trabeculae. Pacemaker 100 may include a set of active fixation tines as disclosed in commonly-assigned, pre-grant publication U.S. 2012/0172892 (Grubac, et al.), hereby incorporated herein by reference in its entirety. Pacemaker 100 may further include a delivery tool interface 158. Delivery tool interface 158 is located at the proximal end of pacemaker 100 and is configured to connect to a delivery device, such as a catheter, used to position pacemaker 100 at an implant location during an implantation procedure, for example within a heart chamber.

Fixation tines 166 are configured to anchor pacemaker 100 to position electrode 164 in operative proximity to a targeted tissue for delivering therapeutic electrical stimulation pulses.

Numerous types of active and/or passive fixation members may be employed for anchoring or stabilizing pacemaker 100 in an implant position.

Pacemaker 100 includes a coupling member 180 for coupling a trigger signal from emitting device 18 to a receiving transducer enclosed within housing 150. For example, coupling member 180 may be an acoustic coupling member for transferring sound waves to an acoustic receiving transducer (not shown) enclosed within housing 150 along an inner surface of coupling member 180. In another example, coupling member 180 may be a transparent window for transferring light emitted by emitting device 18 to an optical receiving transducer enclosed within housing 150 along an inner surface of member 180.

Figure 5:
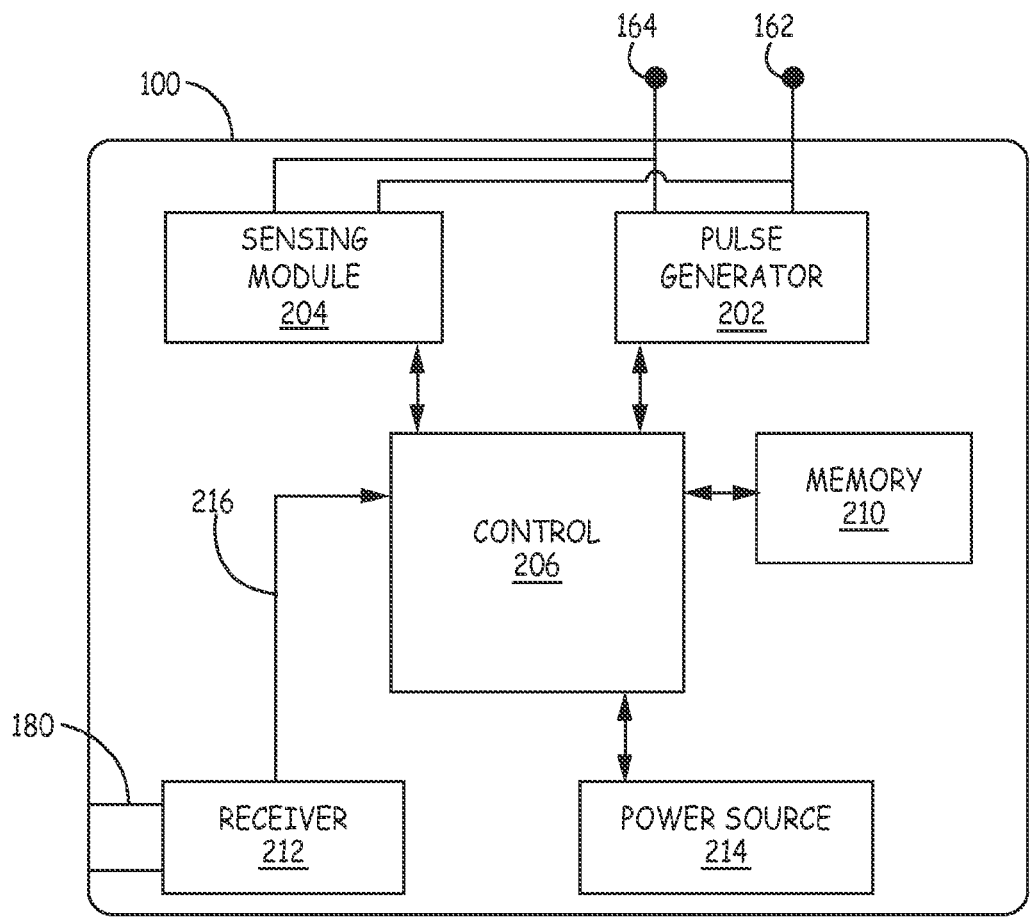
FIG. 5 is a functional block diagram of an example configuration of the pacemaker of FIG. 4.

FIG. 5 is a functional block diagram of an example configuration of pacemaker 100. Pacemaker 100 includes a pulse generator 202, an optional sensing module 204, a control module 206, memory 210, trigger signal receiver 212 and a power source 214. Pulse generator 202 generates electrical stimulation pulses that are delivered to heart tissue via electrodes 162 and 164. Control module 206 controls pulse generator 202 to deliver a stimulation pulse in response to receiving a trigger detect signal 216 from receiver 212. In other embodiments, pulse generator 202 may be configured to be enabled to deliver a stimulation pulse directly by an input signal received from receiver 212. For example, a switch responsive to a trigger detect signal produced by receiver 212 may enable pulse generator 202 to deliver a stimulation pulse to a targeted tissue via electrodes 162 and 164.

Pulse generator 202 includes one or more capacitors and a charging circuit to charge the capacitor(s) to a pacing pulse voltage. The pacing capacitor may be charged to the pacing pulse voltage while control module 206 waits for a trigger detect signal 216 from receiver 212. Upon detecting the trigger signal, the capacitor is coupled to pacing electrodes 162, 164 to discharge the capacitor voltage and thereby deliver the pacing pulse. Alternatively, detection of the trigger signal initiates pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in pacemaker 100 for charging a pacing capacitor to a predetermined pacing pulse amplitude under the control of control module 206 and delivering a pacing pulse. Alternatively, pulse generator 202 may include a switch that connects power source 214 to pacing electrodes 162 and 164 to deliver the pacing pulse.

Receiver 212 receives trigger signals through coupling member 180. Receiver 212 includes one or more receiving transducers, which may be mounted directly along an inner surface of coupling member 180, e.g. for receiving sound waves or light. The trigger signal causes a receiving transducer to produce a voltage signal that is passed to a comparator included in receiver 212 (or control module 206) for comparison to a trigger signal detection threshold. If the voltage signal produced by the receiving transducer is greater than the detection threshold, a trigger detect signal 216 is passed to control module 206, or directly to pulse generator 202, to cause pacing pulse delivery.

In some examples, pulse generator 202 is enabled to deliver a pacing pulse immediately upon receiving a trigger detect signal 216, either directly from receiver 212 or via control module 206. Alternatively, the pacing pulse may be delivered after a predetermined time delay. In either case, the system controls the delivery of a pacing pulse by pacemaker 100 to occur at a desired time interval following a sensed event. For example, ICD 14 may sense a P-wave using the techniques disclosed herein and a trigger signal may be sent to the pacemaker 100 at a desired AV interval less any inherent system delays to cause the pacemaker 100 to deliver a pacing pulse at the desired AV interval, such as is generally disclosed in U.S. Provisional Pat. No. 61/989,123 (O'Brien, et al.), in U.S. Provisional Pat. No. 61/989,114 (Cinbis, et al.), and U.S. Provisional Pat. No. 61/989,302 (Carney, et al.), which are incorporated herein by reference in their entirety.

In some examples, pacemaker 100 is solely a therapy delivery device without sensing capabilities. In other examples, pacemaker 100 may include a sensing module 204 coupled to electrodes 160 and 162 for sensing near-field EGM signals for use in controlling the delivery of pacing pulses. For example, when pacemaker 100 is implanted in the LV, R-waves in the LV may be sensed by sensing module 204. Sensing module 204 generates an R-wave sense signal that is provided to control module 206. Control module 206 may start a pacing timing interval upon receiving a trigger detect signal 216 from receiver 212. If an R-wave sense signal is received by control module 206 from sensing module 204 prior to the pacing timing interval expiring, no pacing pulse is delivered by pulse generator 202. If the pacing timing interval expires prior to receiving an R-wave sense signal from sensing module 204, control module 206 enables pulse generator 202 to deliver a pacing pulse.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 5 for the sake of clarity.

Circuitry represented by the block diagram shown in FIG. 5 may include any discrete and/or integrated electronic circuit components that implement analog and/or digital circuits capable of producing the functions attributed to pacemaker 100 herein. The functions attributed to pacemaker 100 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of pacemaker 100 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal received by receiver 212

In one embodiment, pacemaker 100 includes only receiver 212, pulse generator 202 including low voltage charging circuitry and a pacing capacitor, power source 214 and control module 206, which may be implemented as a logic circuit for controlling pacing pulse delivery in response to trigger signal detection. The pacemaker 100 in this example is minimized in size and functionality and does not include sensing module 204 for acquiring physiological signals and does not include an RF transceiver or amplifier included in standard bi-directional telemetry circuitry.

FIG. 6 depicts ECG 200, ECG 210, and ECG 220 recorded simultaneously using subcutaneous (or substernal) electrodes implanted outside the cardiovascular system. The electrodes used to acquire ECGs 200, 210 and 220 may be within or outside the thoracic cavity but are carried by a lead or IMD housing that is extravascular and extracardiac.

ECG 200 is recorded along a lateral vector, e.g. vector 62 shown in FIG. 1 between electrode 30 and housing electrode 15. ECG 210 is recorded along a diagonal vector, e.g. vector 64 shown in FIG. 1 between electrode 28 and housing electrode 15. ECG 220 is recorded along a cranial vector, e.g. vector 60 between electrodes 28 and 30 in FIG. 1.

Cardiac events are indicated on each respective ECG 200, 210 and 220 as P-waves (P) 202, 212 and 222, R-waves (R) 204, 214 and 224, and T-waves (T) 206, 216, and 226, respectively. The non-cranial vectors used to record ECG 200 and ECG 210 are relatively more sensitive to R-waves 204, 214 than P-waves 202, 212 and have a high signal-to-noise ratio for detecting R-waves without oversensing of P-waves 202, 212 or T-waves 206, 216. For example, in lateral ECG 200, the amplitude of R-wave 204 is relatively much higher than the amplitude of T-wave 206 and P-wave 202. An R-wave sensing threshold can be set greater than the amplitudes of P-wave 202 and T-wave 206 that enables reliable sensing of R-waves without sensing P-waves and T-waves.

The cranial vector used to record ECG 220 has a low signal-to-noise ratio for sensing R-waves 224 since the P-waves 222 and T-waves 226 are relatively large compared to R-waves 224. P-waves 222 are larger in the cranial vector ECG 220 than the P-waves 202 and 212 in the non-cranial vector ECGs 200 and 210. Accordingly, P-waves may be most reliably sensed from cranial vector ECG 220. The positive amplitude of R-waves 224 in the cranial vector ECG is much smaller than the positive amplitudes of R-waves 204 and 214 in the non-cranial vector ECGs 200 and 210 (note y-axis scale change in ECG 220). However, since the positive amplitudes of the P-waves 222, R-waves 224 and T-waves 226 in the cranial vector ECG can be relatively similar, rejection of R-waves 224 and T-waves 226 is required in order to positively identify P-waves 222 for use in controlling triggered pacemaker 100. In this example, the amplitude of the P-wave 222 is similar to the amplitudes of the R-wave 224 and T-wave 226 so that a sensing threshold alone may not reliably identify valid P-waves.

Figure 7:
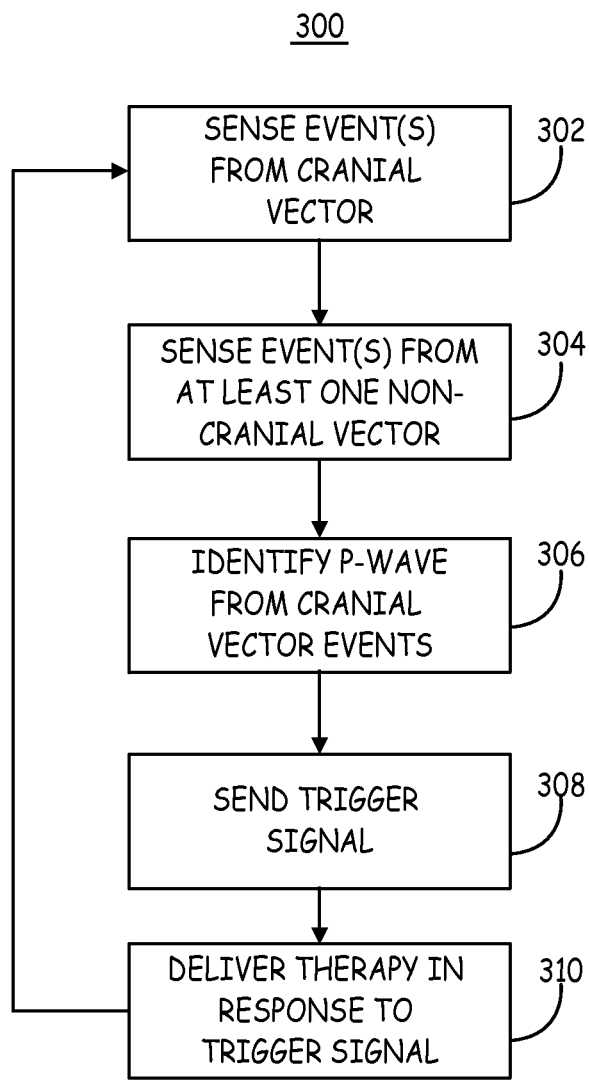
FIG. 7 is a flow chart of a method for controlling a triggered pacemaker according to one embodiment.

FIG. 7 is a flow chart 300 of a method for identifying P-waves for controlling a triggered pacemaker according to one embodiment. The method shown in FIG. 7 for identifying P-waves is performed by the ICD 14 in the illustrative medical device system of FIG. 1. In other examples, another sensing device coupled to extracardiac, non-transvenous electrodes may perform cardiac signal sensing and P-wave identification. At blocks 302 and 304, the ICD electrical sensing module receives cardiac signals from a cranial sensing electrode vector and at least one non-cranial sensing electrode vector. The sensing module may be configured to sense events from the cranial and non-cranial ECG vectors using programmable sensing thresholds, which may be auto-adjusting sensing thresholds, e.g. as disclosed in U.S. Pat. No. 5,117,824 (Keimel, et al.), hereby incorporated herein by reference in its entirety, for sensing P-waves and R-waves. The cranial sensing electrode vector may be a vector that is in closest alignment with a cranial-caudal axis of the patient of the available sensing vectors and the non-cranial vector may be the vector that is in closest alignment with a transverse plane of the patient. Alternatively, the non-cranial vector may be any vector other than the cranial vector. The cranial vector is assumed to have the closest alignment with a vector along which P-waves have the highest amplitude relative to R-waves and T-waves compared to other available vectors.

A first sensing threshold is applied to the cranial vector at block 302 to sense events that include P-waves. Since the P-wave amplitude may be similar to R-waves and T-wave amplitudes, events sensed from the cranial vector may include R-waves and T-waves, i.e. non-P-wave events, in addition to valid P-waves.

A second sensing threshold is applied to at least one non-cranial vector at block 304 for sensing ventricular events. The non-cranial vector is assumed to have the closest alignment with a vector along which R-waves have the highest amplitude relative to P-waves compared to other available vectors. The second sensing threshold may be an auto-adjusting threshold. The second sensing threshold is set greater than the amplitude of P-waves that may be present in the non-cranial vector to avoid P-wave sensing. The second sensing threshold may intentionally be set lower than the T-wave amplitude to enable sensing of both R-waves and T-waves in the non-cranial ECG.

In the illustrative embodiment of FIG. 1, three ECG vectors may be used to sense cardiac event signals, the cranial vector 60, the lateral vector 62 and the diagonal vector 64. A unique sensing threshold, which may be an auto-adjusting or non-adjusting sensing threshold may be applied to each respective ECG vector for sensing events from that ECG vector. The sensing threshold applied to the cranial ECG vector will be below expected P-wave amplitudes and alone will not distinguish between ventricular events (R-waves and T-waves) and atrial events (P-waves). The sensing threshold applied to the transverse and diagonal ECG vectors is intended to exclude P-wave sensing but may include T-wave sensing on one or both of these non-cranial vectors.

At block 306, the ICD processor (or cardiac signal analyzer) identifies P-wave events from the cranial ECG vector using the non-cranial ECG vectors for rejecting non-P-wave events or isolating valid P-wave events. In one example, events sensed from the cranial vector that occur simultaneously with events sensed from at least one non-cranial vector are rejected as non-P-wave events.

In another example, identifying P-wave events at block 306 may include setting a P-wave sensing window that is applied to the cranial ECG vector. The P-wave sensing window is set based on events sensed from the non-cranial ECG vector. P-wave sensing threshold crossings during the sensing window are sensed as P-wave events. The P-wave sensing window may be set to begin a predetermined time interval following an R-wave (or T-wave) sensed from a non-cranial ECG vector and terminated upon sensing a P-wave from the cranial ECG vector or prior to sensing a next R-wave event from the non-cranial vector. In another example, the P-wave sensing window may be set during an interval that no sensing threshold crossings are occurring on the non-cranial ECG vector. Alternatively, a rejection time window or blanking interval that spans a sensed R-wave (and/or T-wave) may be defined by the ICD processor during which any events sensed on the cranial ECG vector are rejected as non-P-wave events.

P-wave identification at block 306 may involve morphology analysis in some examples. A P-wave morphology template may be established by acquiring the cranial ECG vector over a complete cardiac cycle or portion thereof between two consecutively sensed R-waves on a non-cranial ECG vector. A P-wave portion may be identified based on peak amplitude, slope, time relative to an R-wave event and/or T-wave event sensed on a non-cranial ECG, or other morphological features or combinations of features. The template of the P-wave portion may be stored for performing morphological comparisons between unknown sensed events and the stored template. When a morphology match occurs, the unknown sensed event is identified as a P-wave. A morphology matching window may be set based on sensing ventricular events on a non-cranial ECG. During the morphology matching window, the cranial ECG is sampled and sample points are analyzed according to the implemented morphology matching algorithm.

A P-wave template may be a waveform template for performing waveform analysis, such as a wavelet analysis as generally disclosed in U.S. Pat. No. 6,393,316 (Gillberg, et al.), hereby incorporated herein by reference in its entirety. In other examples, the P-wave template may be one or more representative morphology features determined and stored for distinguishing P-waves from R-waves and T-waves. Other methods that could be used to establishing a P-wave template may correspond to the techniques disclosed in U.S. Pat. No. 5,312,445 (Nappholz, et al.). In other examples, without any limitation intended, amplitude, slope, number of peaks, number of inflection points, and signal width are features that are among the representative morphology features that may be used for identifying P-waves.

Once the P-wave morphology template is established using a time interval set based on non-cranial ECG vector events, only the cranial ECG vector may be acquired for identifying P-waves. Alternatively, a non-cranial ECG vector may continue to be used to set a P-wave window on a beat-by-beat basis that is applied to the cranial ECG vector during which morphology template matching and/or feature comparisons are performed.

P-wave events are identified at block 306 as they occur in real time such that upon identifying a P-wave from the cranial ECG vector, the ICD enables the emitting device to send a trigger signal at block 308. The intracardiac pacemaker receives the trigger signal at block 310 and in response to detecting the trigger signal delivers a pacing pulse to the ventricle. The pacing pulse is delivered at a desired AV interval following the sensed P-wave by controlling the timing of the trigger signal following the sensed P-wave and/or controlling the timing of the pacing pulse after detecting the trigger signal.

Figure 8:
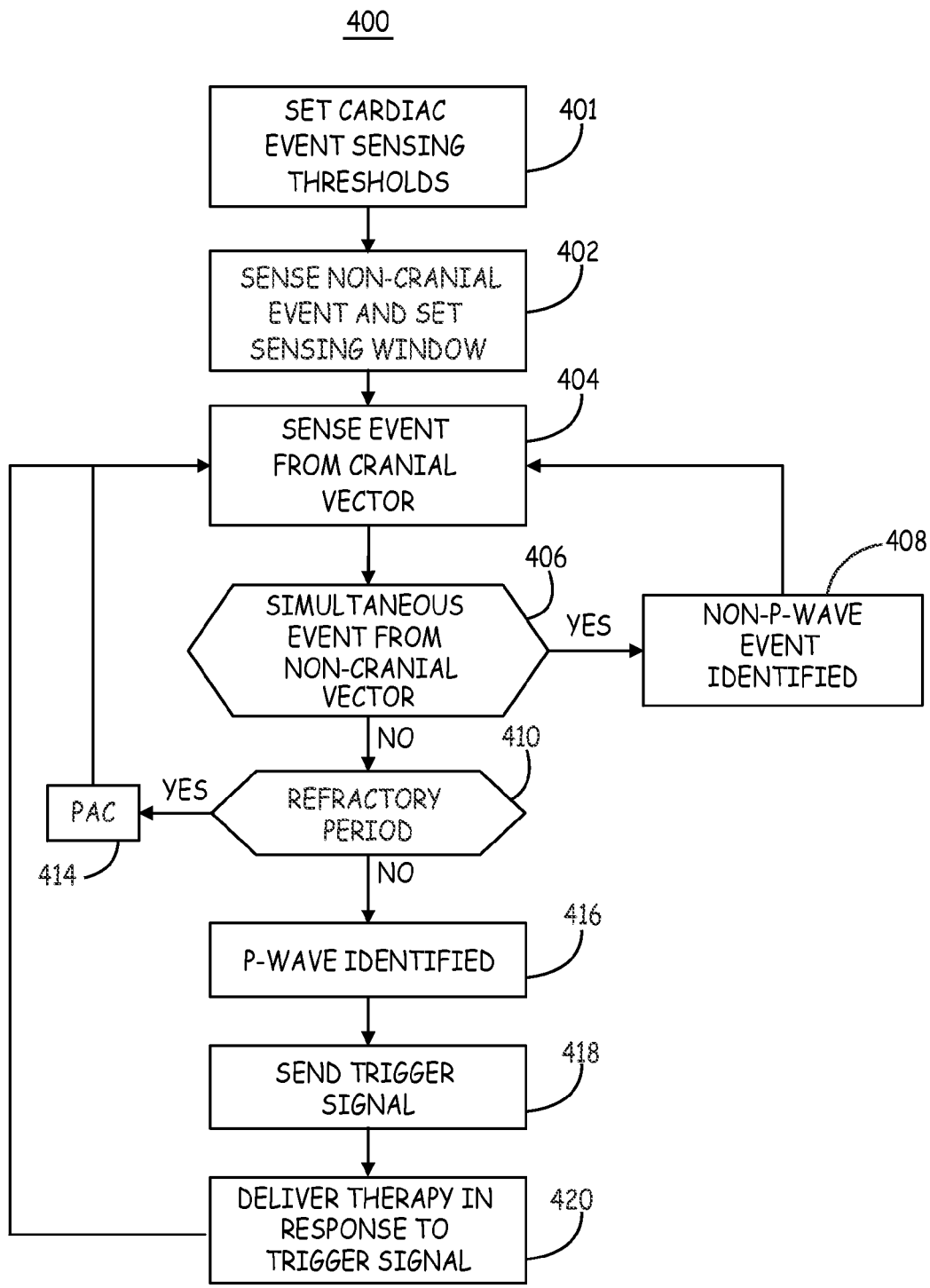
FIG. 8 is a flow chart of a method for identifying P-waves from a cranial ECG vector according to one embodiment.

FIG. 8 is a flow chart 400 of a method for identifying P-waves from a cranial ECG vector according to one embodiment. At block 401, cardiac event sensing thresholds are set for a cranial ECG vector and for one or more non-cranial ECG vectors. For example, a P-wave sensing threshold may be set for the cranial ECG vector. Whenever the cranial ECG vector crosses the sensing threshold an event is sensed at block 404. However, since the P-wave may have an amplitude that is similar to T-waves and/or R-waves on the cranial ECG vector, T-waves and/or R-waves may be oversensed as P-waves.

Accordingly, other sensing threshold(s) may be set at block 402 that are applied to a lateral and/or a diagonal ECG vector for sensing R-waves and T-waves. One sensing threshold may be used such that both R-waves and T-waves are sensed but not P-waves. Alternatively, two sensing thresholds may be set such that if the first lower threshold is crossed but not the second higher threshold, then the event is sensed as a T-wave. If the second higher threshold is crossed, then the event is sensed as an R-wave. Sensing thresholds are set for the lateral and/or diagonal vectors to promote accurate sensing of non-P-wave events (e.g. R-waves and/or T-waves) that are expected to be oversensed as P-waves on the cranial sensing vector without oversensing P-waves on the non-cranial vectors.

In this example and other examples presented herein, the cranial ECG vector is assumed to have the highest P-wave amplitude relative to other cardiac event amplitudes out of the possible ECG vectors available. In other words, a ratio of P-wave amplitude to R-wave amplitude is highest in the cranial ECG vector compared to other vectors. It is recognized that in different embodiments, depending on the electrode and lead configurations used and implant locations of the electrodes relative to each other and the heart, a non-cranial ECG vector may contain the highest P-wave amplitude to R-wave amplitude ratio. If this is the case, it is to be understood that the ECG vector having the highest P-wave amplitudes is selected for sensing P-waves and another ECG vector having relatively lower P-wave amplitudes is used for isolating P-waves or rejecting non-P-wave events from the selected ECG vector.

Referring again to the example of FIG. 8, simultaneous monitoring of the cranial ECG vector and at least one of the lateral or diagonal vectors is performed for sensing and identifying P-waves. At block 402, a P-wave sensing window is optionally set. The P-wave sensing window may be started in response to sensing an event, e.g. an R-wave or T-wave from a non-cranial ECG vector. The P-wave sensing window may be terminated after a predetermined interval of time which may be based on previously measured PR or RR intervals. Alternatively the P-wave sensing window is a variable duration window that is terminated upon identifying the first P-wave event occurring after the R-wave or T-wave that started the P-wave sensing window. Any cranial ECG sensing threshold crossing that occurs outside the P-wave sensing window is not sensed as a P-wave.

When an event is sensed on the cranial ECG vector at block 404 (during the P-wave sensing window if set), the processor determines if another sensed event occurred simultaneously on a non-cranial vector at block 406. "Simultaneous sensed events" as used herein may refer to events sensed within a pre-determined time interval of each other, e.g. within approximately 50 ms (or a lower range limit) of each other.

If a simultaneous event is sensed on a non-cranial vector, the event sensed on the cranial vector is determined to be a non-P-wave event at block 408 and is ignored for the purposes of triggering the intracardiac pacemaker to deliver an atrial-synchronized ventricular pacing pulse. If no simultaneous event is sensed on a non-cranial vector (block 406), a determination is made at block 410 whether the sensed event on the cranial vector occurred during a refractory sense period.

A refractory sense period may be applied to prevent trigger signals from being emitted due to sensing a premature contraction, such as a premature atrial contraction (PAC) or premature ventricular contraction (PVC). The refractory sense period may be started upon an identified P-wave. If a cranial vector event is not sensed simultaneously with a non-cranial vector event at block 406, but does occur during a refractory sense period at block 410, the event is detected as a PAC at block 412. A PVC would likely be sensed simultaneously on both the non-cranial vector and the cranial vector and would thus be rejected at block 406.

If the sensed event on the cranial vector is outside the refractory sense period and not simultaneously sensed with an event on the non-cranial vector, it is identified as a P-wave at block 416. A trigger signal is sent at block 418 by the emitting device under the control of the ICD. The ICD timing circuit sends a control signal to the drive circuit of the emitting device to cause a trigger signal to be emitted for detection by the intracardiac pacemaker. At block 420, the pacemaker delivers at least one pacing pulse in response to detecting the trigger signal.

Figure 9:
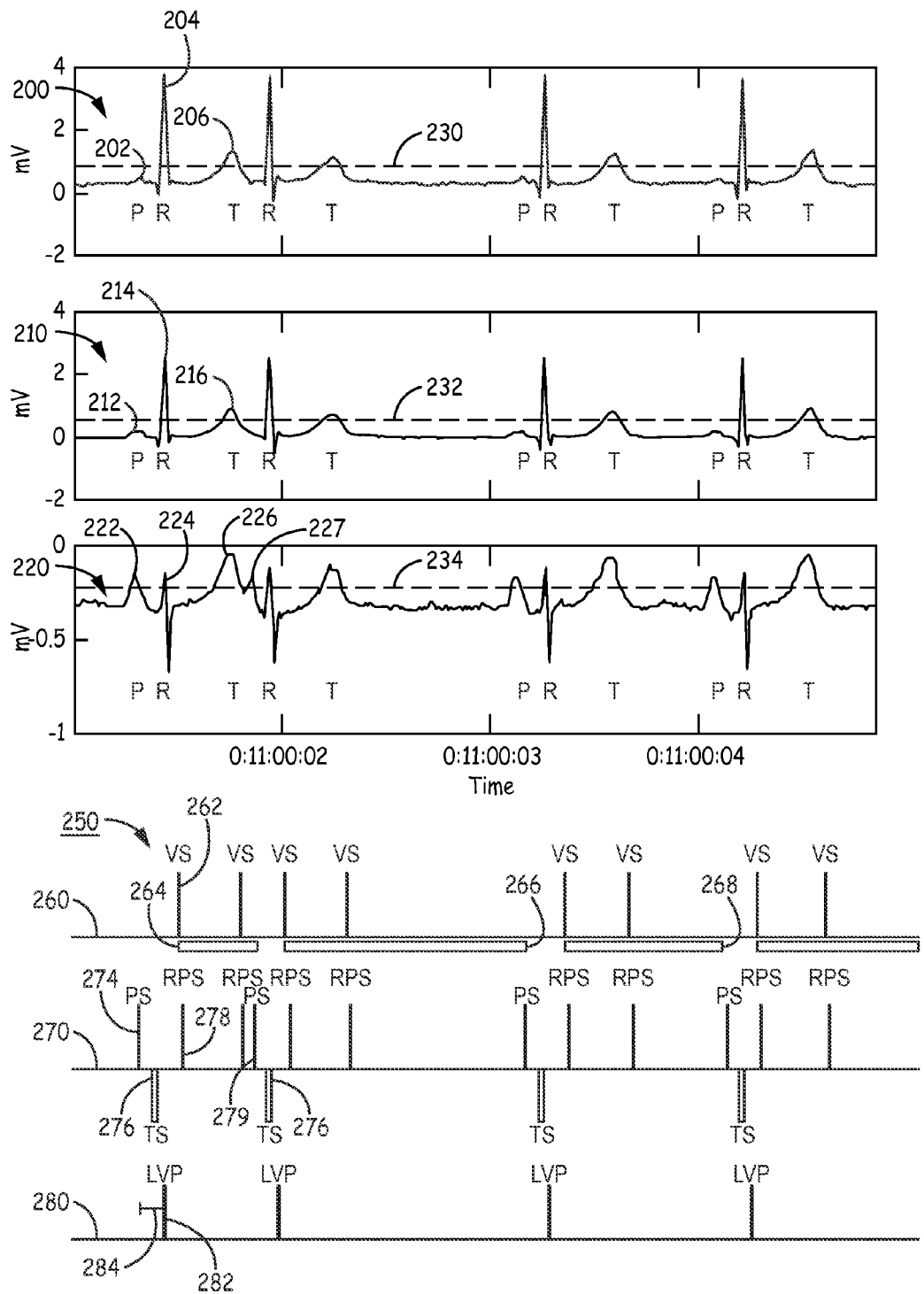
FIG. 9 shows the sample ECG recordings of FIG. 6 with a timing diagram depicting events sensed by the ICD, trigger signals sent by the emitting device, and resulting pacing pulses delivered by the triggered pacemaker.

FIG. 9 shows the sample ECGs 200, 210 and 220 of FIG. 6 with a timing diagram 250 depicting events sensed by the ICD, trigger signals sent by the emitting device, and resulting pacing pulses delivered by the triggered pacemaker. As described previously, the lateral ECG 200 is characterized by a high signal-to-noise ratio between R-waves 204 and P-waves 202 for reliably sensing R-waves. A sensing threshold 230 may be set at an amplitude that reliably discriminates R-waves 204 and T-waves 206 from P-waves 202. Sensing threshold 230 is set low enough to cause sensing of both R-waves 204 and T-waves 206 based on a sensing threshold crossing.

Similarly, a sensing threshold 232 may be applied to diagonal vector 210 that will result in sensing of R-waves 214 and T-waves 216 without sensing P-waves 212. Alternatively, a second higher sensing threshold may be applied to ECG 200 and/or ECG 210 to sense R-waves distinctly from T-waves based on the higher threshold crossing.

The sensing threshold 234 applied to the cranial vector 220 that enables P-waves 222 to be sensed, however, will result in oversensing of both R-waves 224 and T-waves 226. Using the method generally described in conjunction with flow chart 400 of FIG. 8, one or both of the lateral ECG 200 and diagonal ECG 210 may be monitored for sensing R-waves and T-waves.

A non-cranial ECG marker channel 260 is shown in timing diagram 250. Sensed events 262 are labeled as ventricular sensed (VS) events since these events could be R-waves or T-waves but are both ventricular signals, i.e. non-P-wave signals. A cranial ECG vector marker channel 270 shows P-wave sense (PS) events 274 corresponding to P-waves 222. The PS events 274 are sensed without a simultaneous VS event on the non-cranial marker channel.

Variable length P-wave sensing windows 264, 266, 268 are shown along marker channel 260. A P-wave sensing window 264 is started upon a VS event 262, which may be an R-wave that has been sensed on a non-cranial vector based on an R-wave sensing threshold. The next event sensed is a T-wave 216, which is simultaneously sensed on both the cranial and non-cranial vectors and is therefore a rejected P-wave sense event (RPS) 278 even though it occurs during the P-wave sensing window 264. The P-wave sensing windows 264, 266, and 268 may alternatively begin later in the cardiac cycle after a VS event based on recently measured RR or PR intervals or following a T-wave rejection refractory period following the VS event 262. A T-wave rejection refractory period may be set based on an expected R-T interval, which could be measured from previously sensed ventricular cardiac cycles between sequential R-wave and T-wave sensed events or set as a portion of previously sensed RR intervals.

The next event sensed on the cranial vector is a P-wave 227. Since it is not sensed simultaneously with a non-cranial VS event, and occurs during the P-wave sensing window, it is identified as a PS event 279 and causes a trigger signal (TS) 276 to be emitted. The first PS event 279 during the P-wave sensing window 264 terminates the P-wave sensing window 264.

The next VS event after window 264 starts a new P-wave sensing window 266 that is terminated by the next PS event. Any events sensed during the windows 264, 266, 268 that are sensed simultaneously on both a cranial and non-cranial ECG vector are RPS events. The first cranial ECG event sensed during the P-wave sensing windows 264, 266, 268 that is not simultaneous with a non-cranial ECG sensed event is identified as a PS event, which terminates the P-wave sensing window. The next P-wave sensing window is started on the next VS event (or after the VS event based on recent RR and/or PR intervals). The variable duration P-wave sensing window accounts for changes in the cardiac cycle length. In other examples, the P-wave sensing window is a predetermined duration that is set based on previously measured PR and/or RR intervals. The P-wave sensing window is optional.

The emitting device is controlled to emit a trigger signal (TS) 276 in response to the identified PS events 274. The intracardiac pacemaker delivers an LV pacing pulse (LVP) 282, shown on time line 280, in response to detecting the TS 276. The LVP 282 is delivered at a desired AV interval 284 following the PS event 274 as controlled by the timing of the TS 276 taking into account any system delays.

Rejected P-wave sense (RPS) events 278 are events sensed on the cranial ECG vector 220 based on crossings of the P-wave sensing threshold 234 that occur simultaneously with a VS event 262 on the non-cranial marker channel 260. The RPS events 278 are identified as events sensed on the cranial ECG vector that are ventricular events, i.e. R-waves or T-waves, and are therefore rejected for the purposes of triggered pacing. No TS is emitted following RPS events 278, and no LVP is delivered following RPS events 278. In this way, the triggered pacemaker is controlled to deliver pacing pulses 282 at a desired pacing interval 284 using a first subcutaneous or sub-sternal ECG vector for sensing P-waves and a second subcutaneous or sub-sternal ECG vector for rejecting P-wave sensed events from the first ECG vector that are oversensed R-waves and T-waves to thereby promote proper AV synchronized pacing.

Figure 10:
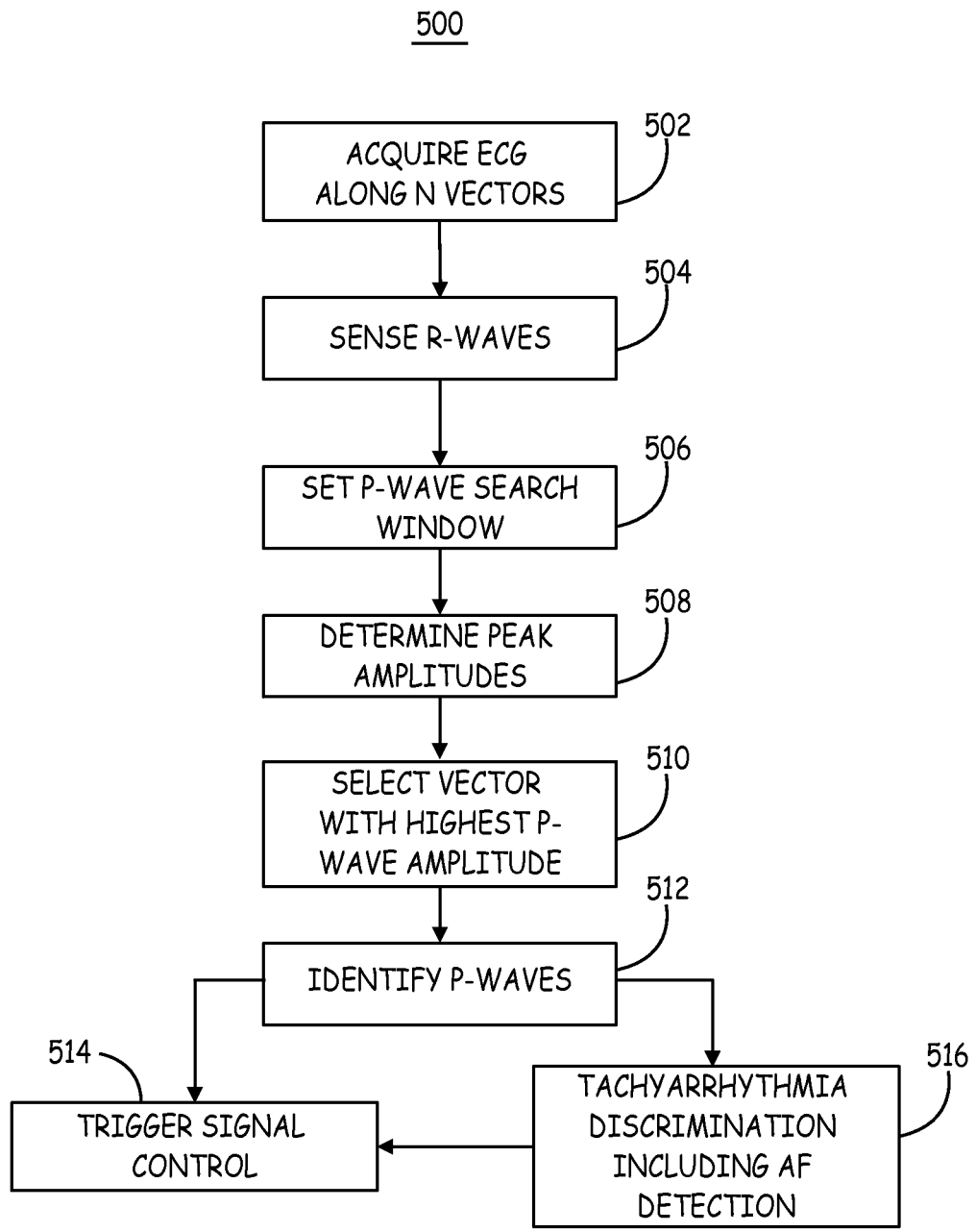
FIG. 10 is a flow chart of a method for identifying a vector that provides the highest P-wave amplitude for sensing P-wave events and controlling a trigger signal sent to an intracardiac pacemaker.

FIG. 10 is a flow chart of a method 500 for identifying a vector that provides the highest P-wave amplitude for sensing P-wave events and controlling a trigger signal sent to an intracardiac pacemaker. At block 502, cardiac signals are acquired using two or more sensing vectors selected from the available electrodes. In some cases, the sensing vector that provides the highest P-wave amplitude or greatest ratio between P-wave and R-wave amplitudes is unknown. For example, two or more vectors may be within an acute angle of a cranial-caudal axis of the patient and the vector having the greatest P-wave amplitude may be unknown. While a vector most closely aligned with a cranial-caudal axis of the patient is expected to provide the greatest P-wave amplitude, this may not always be the case depending on the particular electrode locations, patient anatomy, etc. As such, cardiac signals may be acquired from multiple ECG vectors at block 502 for a comparative analysis to determine which vector provides the greatest P-wave amplitude or greatest P-wave to R-wave amplitude ratio. Although not shown in the flow chart, it should be understood that signal processing may be performed on the acquired cardiac signals to generate ECG signals—examples of such signal processing techniques are described in the '153 patent.

R-waves are sensed from each ECG signal at block 504. R-waves may be sensed using an auto-adjusting sensing threshold or other previously established R-wave sensing threshold, which may be a user-programmed value. A P-wave search window is set at block 506 prior to the R-wave sense signal (in contrast to a P-wave sensing window set after an R-wave sense signal during real-time P-wave sensing for trigger signal control). The P-wave search window may be set individually for each ECG signal based on the time of the sensed R-wave of the respective ECG signal. Alternatively, a P-wave search window may be set for all N ECG signals based on an earliest occurring R-wave sense signal.

In one embodiment, each of the N ECG signals is sampled and buffered over a predefined P-wave search window duration. The sample points may be stored in a memory buffer. For example, each ECG signal may be sampled and stored using a 300 ms buffer. Upon an R-wave sense signal, the highest amplitude stored in the 300 ms buffer (preceding the R-wave sensing threshold crossing) is determined as the peak amplitude of the P-wave at block 508. In some examples, a QRS blanking period may be applied at the end of the buffered sample points, just prior to the R-wave sense signal, to ignore signal sample points that may be part of the QRS signal of the ECG signal.

The criteria for selecting a vector for identifying P-waves from multiple available sensing vectors may be based on the highest P-wave amplitude. Alternatively, selection of a vector for identifying P-waves may be based on the highest P-wave amplitude to R-wave amplitude ratio or smallest absolute difference between P-wave amplitude and R-wave amplitude. As such, in some examples peak R-wave amplitudes are determined at block 508 in addition to the P-wave amplitudes. For example, the next peak amplitude after the R-wave sensing threshold crossing may be determined as the peak R-wave amplitude. In some examples, an R-wave window is set following the R-wave sense signal and a peak amplitude during the R-wave window is determined as the peak R-wave amplitude.

The peak amplitudes are determined at block 508 during buffered P-wave search windows for each ECG signal over a "learning period." The learning period may be up to one minute, several minutes or another time period and may include multiple intermittent intervals. At the end of the learning period, the stored peak amplitudes for each ECG vector may be averaged to determine a vector having the highest average P-wave amplitude (or highest average P-wave to R-wave amplitude ratio) at block 510. The vector having the highest P-wave amplitude (or highest P-wave to R-wave amplitude ratio) is selected as the vector from which P-waves will be identified.

It is further contemplated that the vector selected at block 510 is a virtual vector, which is a mathematical combination of the ECG signals from the actual physical vectors. A method for determining a virtual sensing vector is generally disclosed in U.S. Pat. No. 6,505,067 (Lee, et al.), hereby incorporated herein by reference in its entirety. A virtual vector may be computed from two physical vectors found to have the largest P-wave amplitude, largest P-wave amplitude to R-wave amplitude ratio, or smallest absolute difference between P-wave and R-wave amplitudes in some examples. The P-wave axis corresponding to a maximum P-wave amplitude may be computed based on two physical vectors. The angle of the P-wave axis may then be used to compute a virtual vector. The virtual vector is selected as the vector from which P-waves will be identified.

Additionally, another virtual vector may be computed from two physical vectors found to have the largest R-wave amplitude. A QRS axis (angle at which the highest QRS amplitude occurs) and a P-wave axis (angle at which the highest P-wave amplitude is found) may then be selected for use in identifying P-waves using the techniques described above in conjunction with FIGS. 7 and 8.

At block 512, the selected vector is used to identify P-waves for sending P-wave synchronous trigger signals to an intracardiac pacemaker at block 514 to cause the pacemaker to deliver a pacing pulse at a desired AV interval following an identified P-wave. P-waves may be identified at block 512 using the selected vector and the methods described above in conjunction with FIG. 7 and FIG. 8. For example, P-waves may be identified from events sensed on the selected ECG vector, virtual or physical, by rejecting other sensed events that occur simultaneously with sensed events on a different ECG signal, virtual or physical (e.g. within approximately 50 ms or another predetermined limit of each other).

The process for selecting a vector as described in conjunction with blocks 502 through 510 in flow chart 500 may be repeated periodically to utilize the optimal sensing vector for identifying P-waves. Leads and electrodes may shift over time, be replaced, and/or new leads may be implanted such that the optimal sensing vector (highest P-wave amplitude or highest signal-to-noise ratio) for identifying P-waves may change over time. The process for selecting a vector for P-wave sensing and identification can be operating in the background while trigger signals are being sent based on P-waves being identified from a currently-selected ECG vector such that therapy is not disrupted during the learning period.

A P-wave identification signal produced by the control module in response to an identified P-wave is provided as input to the timing circuit 92 (FIG. 3) for controlling trigger signal emission by emitting device 18 at block 514. P-wave identification signals produced at block 512 may additionally be provided as input to tachyarrhythmia detector 94 of cardiac signal analyzer 90 (FIG. 3). P-wave identification signals may be used by a tachyarrhythmia detection algorithm for discriminating between supraventricular tachycardia (SVT) and ventricular tachycardia (VT) at block 516. For example, the ratio between the number of identified P-waves on the selected vector and the number of R-waves sensed on a different sensing vector, PR intervals, and/or PP intervals may be used in combination with RR interval and/or R-wave morphology data according to an implemented tachyarrhythmia detection and discrimination algorithm.

In one example, tachyarrhythmia detection may include atrial fibrillation (AF) detection at block 516. P-wave identification signals may be tracked and the disappearance of P-wave identification signals with detection of irregular RR intervals may lead to AF detection. The P-wave identification signals are produced based on methods described above using a cranial or other selected ECG vector having maximum P-wave amplitude. RR intervals are determined from a non-cranial or other selected ECG vector having a maximum R-wave amplitude.

Outcome of tachyarrhythmia discrimination by cardiac signal analyzer 90 at block 516 may be used as input to the timing circuit 92 for controlling trigger signal emission at block 514. For example, timing circuit 92 may control the trigger signal emitting device 18 to emit P-wave asynchronous trigger signals when AF is detected to maintain a desired ventricular rate. Timing circuit 92 may control the trigger signal 18 to emit trigger signals according to an anti-tachycardia pacing therapy in response to detecting VT, which may be synchronized to identified P-waves.

Figure 11:
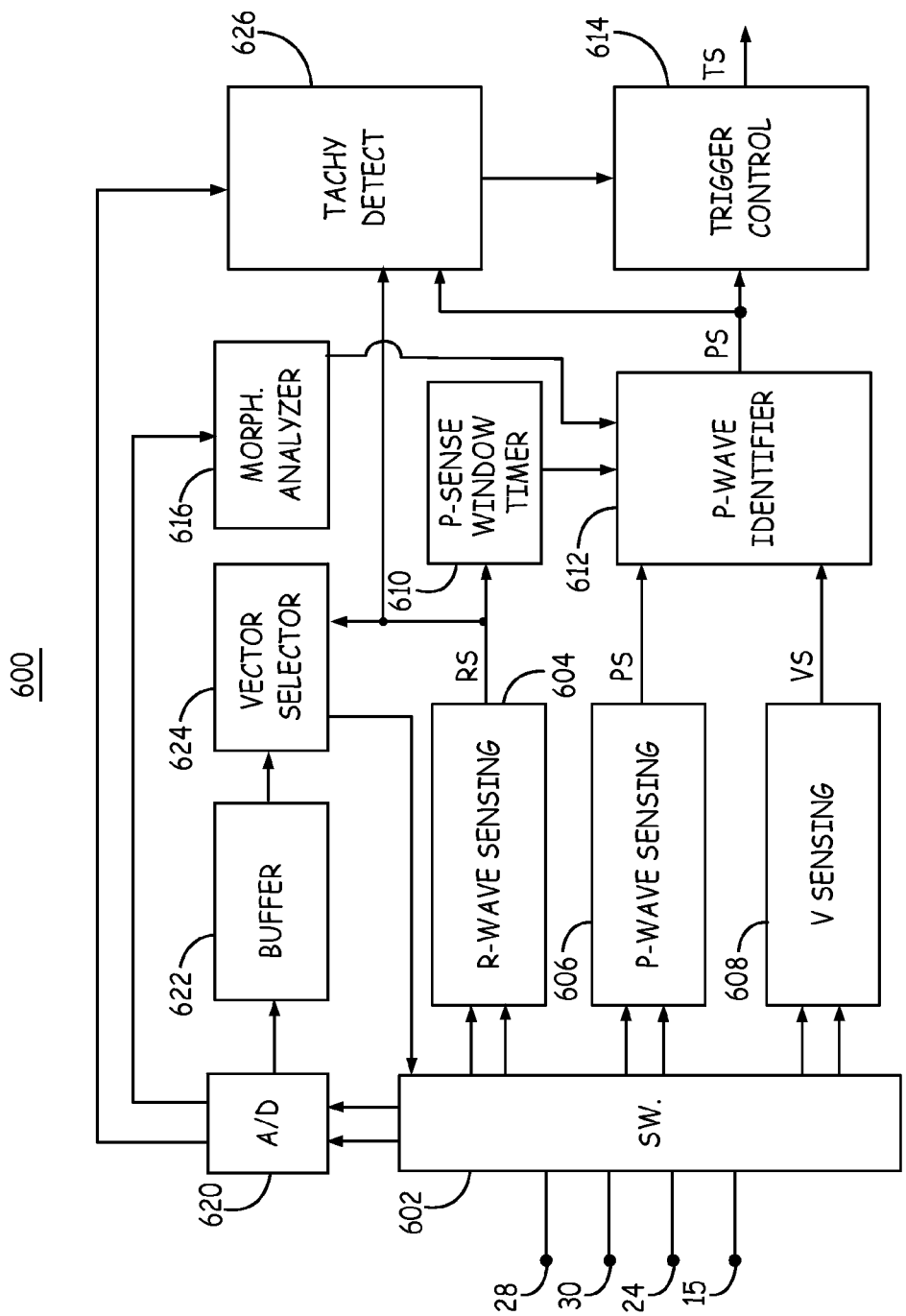
FIG. 11 is a conceptual block diagram of operations performed by an ICD for identifying P-waves and controlling trigger signal emission according to one example.

FIG. 11 is a conceptual block diagram of operations performed by ICD 14 for identifying P-waves and controlling trigger signal emission according to one example. Multiple sensing channels 604, 606, and 608 receive input from electrodes 24, 28, 30 and housing electrode 15 via switching circuitry 602. Switching circuitry 602 and sensing channels 604, 606, and 608 are included in electrical sensing module 86 of FIG. 3. Switching circuitry 602 selects which of electrodes 24, 28, 30, and 15 are coupled to the various sensing channels 604, 606, 608, e.g. under the control of processor 80 (not shown in FIG. 11).

Each sensing channel 604, 606, and 608 includes a filter to improve signal-to-noise ratio and a sense amplifier for sensing events from the sensed cardiac signals. R-wave sensing channel passes R-wave sense signals (RS) to a P-wave sensing window timer 610, P-wave identifier 612, and tachyarrhythmia detection module 626, all of which may be included in cardiac signal analyzer 90 of FIG. 3. P-wave sensing window timer 610 may start a P-wave sensing window at or a predetermined interval after receiving the RS signal.

P-wave identifier 612 receives P-wave sensing (PS) signals from P-wave sensing channel 606. The PS signals received from P-wave sensing 606 will likely include oversensed R-waves and T-waves. P-wave identifier 612 may identify true P-waves from the PS signals received from sensing channel 606 based on an occurrence of a PS signal during the P-wave sensing window set by timer 610. Additionally or alternatively, P-wave identifier 612 may receive ventricular sense (VS) signals from a ventricular sensing channel 608 configured to pass VS signals upon sensing both T-waves and R-waves. If a PS signal is received simultaneously with a VS signal, the PS signal is rejected. In some examples, PS signals are rejected if received simultaneously with a VS signal or received outside a P-wave sensing window (whether simultaneously with a VS signal or not).

P-wave identifier 612 may additionally receive input from morphology analyzer 616. Morphology analyzer 616 may receive one or more digitized ECG signals from analog-to-digital converter 620. Analog-to-digital converter 620 receives a raw cardiac signal from selected electrodes 24, 28, 30 and 15 via switching circuitry 602. Morphology analyzer 616 may provide a P-wave morphology matching score or other comparative index indicative of a morphological feature of true P-waves. When criteria for identifying a true P-wave, which may include a morphology matching score, are satisfied, a PS signal is passed to trigger control 614. Only PS signals identified as true P-waves by identifier 612 are passed to trigger signal control 614. Trigger signal control 614 may be included in timing circuit 92 of FIG. 3 for controlling emitting device 18. It is expected that fewer PS signals are output from P-wave identifier 612 than from P-wave sensing channel 606. P-wave identifier 612 acts as a filter for rejecting non-P-wave events and isolating true P-waves using a sensing window set by timer 610, simultaneous VS signals from ventricular sensing channel 608, and/or morphology matching scores received from morphology analyzer 616.

The P-wave sensing window is set and the VS signals are produced from an ECG signal received by R-wave sensing channel 605 and V sensing channel 608 that is a different ECG signal than P-wave sensing channel 606. For example, a cranial ECG vector is received by P-wave sensing channel 606. A non-cranial ECG vector having the highest signal-to-noise ratio for sensing R-waves is received by R-wave sensing channel 605, and a non-cranial ECG vector having the highest signal-to-noise ratio for sensing R-wave and T-waves is received by V sensing channel 608.

V sensing channel 608 and R-wave sensing channel 604 may receive cardiac signals from the same sensing vector selected from electrodes 24, 28, 30 and 15 or a different sensing vector. When the same sensing vector is used, two different sensing thresholds may be applied for producing RS signals (a relatively higher threshold) and VS signals (a relatively lower threshold) to distinguish R-waves from T-waves. Alternatively or additionally, the V sensing channel 608 and the R-wave sensing channel 604 may use different filters. The R-wave sensing channel 604 may use a higher high-pass corner than the VS sensing channel 608.

In an alternative embodiment, a post-ventricular T-wave rejection refractory period is applied after an RS signal to extend through an expected R-T interval. The T-wave rejection refractory period may be applied by the P-wave identifier 612 to reject PS signals received from P-wave sensing channel 606 during the refractory period. Rejected PS signals during a refractory period following an RS signal are highly likely to be T-waves. The T-wave rejection refractory period may be set based on RT interval measurements between an RS signal from R-wave sensing channel 605 and the next VS signal from V sensing channel 608. In some examples, if a refractory period is used to reject T-waves following an RS signal, V sensing channel 608 may be omitted. The T-wave rejection refractory period may be set to a nominal value or based on previously measured RR intervals, RT intervals and/or RP intervals.

Analog-to-digital converter 620 may pass a digitized ECG signal to a P-wave search buffer 622 that stores signal sample points for a P-wave search window used by vector selector 624. Vector selector 624 and buffer 622 may be included in processor 80 and associated memory 82 shown in FIG. 3. Vector selector 624 receives the RS signals from R-wave sensing channel 604. Upon receiving an RS signal, vector selector 624 retrieves the buffered signal sample points over the search window from buffer 622 and determines a maximum amplitude during the search window, prior to the RS signal, as the P-wave amplitude.

Vector selector 624 analyzes multiple ECG signals (sequentially or simultaneously) as described in conjunction with flow chart 500 of FIG. 10 for selecting the optimal ECG vector for P-wave sensing. Vector selector 624 provides a feedback signal to switching circuitry 602 for selecting the optimal ECG vector for coupling to P-wave sensing channel 606. Vector selector 624 may operate periodically to select an optimal ECG vector for P-wave sensing while P-wave identifier 612 continues to operate using PS signals produced by P-wave sensing channel 606 using a currently selected ECG vector. If an ECG vector having higher P-wave amplitude is identified, switching circuitry 602 is controlled to switch the electrodes coupled to P-wave sensing channel 606.

As described previously, vector selector 624 may perform comparative analysis of multiple ECG vectors for selecting the ECG vector having the highest R-wave amplitude for coupling to R-wave sensing channel 604 and/or an ECG vector that is the most reliable for sensing ventricular events (R-waves and T-waves) for coupling to V sensing channel 608.

Tachyarrhythmia detector 626, which may correspond to tachyarrhythmia detector 94 in FIG. 3, receives RS signals from R-wave sensing channel 604 and may receive PS signals from P-wave identifier 612 for use in detecting and discriminating ventricular fibrillation, VT and SVT based on cardiac intervals according to an implemented detection algorithm. As described above, the disappearance of PS signals from P-wave identifier may be used in detecting AF. Tachyarrhythmia detector 626 may additionally receive digitized ECG signals from ND converter 620 for signal morphology analysis performed in conjunction with cardiac interval-based morphology analysis.

Results of tachyarrhythmia detection by detector 626 may be provided to trigger control 614 for use in controlling a triggered ventricular pacemaker when SVT or VT are detected, e.g. to maintain a regular ventricular rhythm during AF or to delivery anti-tachycardia pacing.

Thus, various examples of a medical device system and associated method for controlling a triggered therapy delivery device have been described according to illustrative embodiments. However, one of ordinary skill in the art will appreciate that various modifications may be made to the described embodiments without departing from the scope of the following claims.

The invention claimed is:

1. A method for controlling automated delivery of therapeutic stimulation pulses by a medical device system including an intracardiac pacemaker implanted in a patient, the method comprising:
    acquiring by an implantable medical device sensing module a first cardiac signal using a first pair of electrodes selected from a plurality of available electrode pairs that are implanted outside the cardiovascular system, the plurality of available electrodes defining at least one sensing vector that is approximately parallel with a cranial-caudal axis of the patient;
    generating a first electrocardiogram (ECG) signal from the received first cardiac signal;
    identifying a P-wave from the ECG signal;
    transmitting a wireless trigger signal from the implantable medical device to the intracardiac pacemaker in response to identifying the P-wave; and
    delivering a pacing therapy by the pacemaker in response to the trigger signal.

2. The method of claim 1, further comprising identifying the P-wave in response to at least one of an amplitude, a frequency content, a number of peaks, a signal width, and a morphology waveform of the ECG signal, wherein the first pair of electrodes defines the at least a first sensing vector that is approximately parallel with the cranial caudal axis.

3. The method of claim 1, further comprising:
    acquiring by the sensing module a second cardiac signal using a second pair of electrodes selected from the plurality of electrodes, the second pair of electrodes defining at least a first sensing vector more closely aligned with a transverse plane of the patient than the first pair of electrodes, wherein the first pair of electrodes defines the first sensing vector that is approximately parallel with the cranial caudal axis;
    generating a second ECG signal from the received second cardiac signal; and
    identifying the P-wave from the first ECG by using the second ECG to reject non-P-wave events in the first ECG.

4. The method of claim 3, further comprising:
    applying a first sensing threshold to the first ECG;
    sensing first events from the first ECG in response to first ECG crossings of the first sensing threshold;
    applying a second sensing threshold to the second ECG;
    sensing second events from the second ECG in response to second ECG crossings of the second threshold;
    identifying first events that are sensed simultaneously with second events; and
    identifying the P-wave from the first ECG by rejecting the first events that are sensed simultaneously with second events.

5. The method of claim 3, further comprising:
    setting a sensing window applied to the first ECG; and
    identifying the P-wave during the sensing window in response to the first ECG crossing a first threshold,
    wherein setting the sensing window comprises:
    applying a second threshold to the second ECG,
    identifying a ventricular event from the second ECG signal in response to the second ECG crossing the second threshold,
    setting the sensing window at a time interval after the identified ventricular event.

6. The method of claim 1, further comprising:
    passing a P-wave sense signal to a tachyarrhythmia detector of the implantable medical device in response to identifying the P-wave;
    detecting a tachycardia in response to the P-wave sense signal;
    controlling the trigger signal in response to detecting the tachycardia.

7. The method of claim 1, further comprising:
    passing P-wave sense signals to a tachyarrhythmia detector of the implantable medical device in response to identifying P-waves from the first ECG;
    detecting atrial fibrillation in response to a disappearance of the P-wave sense signal; and
    controlling the trigger signal in response to detecting atrial fibrillation.

8. The method of claim 1, further comprising:
    determining a P-wave amplitude from each of a plurality of sensing vectors of the plurality of available electrode pairs;
    comparing the P-wave amplitudes; and
    selecting the first pair of electrodes from the plurality of electrode pairs in response to a highest P-wave amplitude.

9. The method of claim 8, further comprising:
    identifying P-waves from an ECG signal generated by the sensing module using a previously selected pair of electrodes;
    transmitting wireless trigger signals in response to identifying the P-waves using the previously selected pair of electrodes; and
    wherein comparing the P-wave amplitudes and selecting the first pair of electrodes is performed during the identifying P-waves from the previously generated ECG signal.

10. The method of claim 1, wherein identifying the P-wave comprises:
    sensing a plurality of events based on threshold crossings of the first ECG signal;
    sensing an R-wave from a second pair of electrodes having at least one electrode that is different from the electrodes in the first pair of electrodes;
    setting a P-wave sensing window in response to the sensed R-wave;
    sensing a T-wave from one of the second pair of electrodes and a third pair of electrodes;
    rejecting ones of the plurality of sensed events that occur outside the P-wave sensing window;
    rejecting ones of the plurality of sensed events that occur simultaneously with the sensed R-wave or the sensed T-wave;
    passing a P-wave sense signal to a trigger signal controller in response to a non-rejected one of the plurality of events; and
    controlling the trigger signal emitting device to emit the wireless trigger signal in response to the trigger signal controller acquiring the P-wave sense signal.

11. An implantable medical device system, comprising:
a first device comprising a sensing module coupled to a plurality of electrodes implanted outside the cardiovascular system of a patient and configured to:
receive by the sensing module a first cardiac signal using a first pair of electrodes of the plurality of electrodes, the plurality of electrodes defining at least a first sensing vector that is approximately parallel with a cranial-caudal axis of the patient;
generate a first electrocardiogram (ECG) signal based on the first cardiac signal;
identify a P-wave using the first ECG signal;
a trigger signal emitting device controlled by the first device to emit a wireless trigger signal in response to the identified P-wave; and
an intracardiac pacemaker configured to detect the wireless trigger signal and deliver a pacing therapy in response to the wireless trigger signal.

12. The device of claim 11, wherein the first device is configured to identify the P-wave in response to at least one of an amplitude, a frequency content, a number of peaks, a signal width, and a morphology waveform of the first ECG signal, wherein the first pair of electrodes defines the first sensing vector that is approximately parallel with the cranial caudal axis.

13. The device of claim 11, wherein the first device is further configured to:
receive by the sensing module a second cardiac signal using a second pair of electrodes of the plurality of electrodes, the second pair of electrodes defining a second sensing vector more closely aligned with a transverse plane of the patient than the first sensing vector, wherein the first pair of electrodes defines the first sensing vector that is approximately parallel with the cranial caudal axis;
generate a second ECG signal based on the second cardiac signal; and
identify the P-wave from the first ECG signal by using the second ECG signal to reject non-P-wave events in the first ECG signal.

14. The device of claim 13, wherein the first device is further configured to:
apply a first sensing threshold to the first ECG signal;
sense first events from the first ECG signal in response to first ECG signal crossings of the first sensing threshold;
apply a second sensing threshold to the second ECG signal;
sense second events from the second ECG signal in response to second ECG signal crossings of the second threshold;
identify first events that are sensed simultaneously with second events; and
identify the P-wave from the first ECG signal by rejecting the first events that are sensed simultaneously with second events.

15. The device of claim 13, wherein the first device is further configured to:
set a sensing window applied to the first ECG signal; and
identify the P-wave during the sensing window in response to the first ECG signal crossing a first threshold,
wherein setting the sensing window comprises:
applying a second threshold to the second ECG signal,
identifying a ventricular event from the second ECG signal in response to the second ECG signal crossing the second threshold,
setting the sensing window at a time interval after the identified ventricular event.

16. The device of claim 13, further comprising:
a tachyarrhythmia detector acquiring a P-wave sense signal in response to identifying the P-wave;
the tachyarrhythmia detector configured to detect a tachycardia in response to the P-wave sense signal;
the first device further configured to control the trigger signal emitting device in response to detecting the tachycardia.

17. The device of claim 11, further comprising:
a tachyarrhythmia detector configured to receive P-wave sense signals in response to P-waves identified from the first ECG signal and detect atrial fibrillation in response to a disappearance of the P-wave sense signal,
wherein the first device is further configured to control the trigger signal emitting device in response to detecting the atrial fibrillation.

18. The device of claim 11, wherein the first device is further configured to:
determine a P-wave amplitude from each of a plurality of sensing vectors of the plurality of available electrode pairs;
compare the P-wave amplitudes; and
select the first pair of electrodes from the plurality of electrode pairs in response to a highest P-wave amplitude.

19. The device of claim 18, wherein the first device is further configured to:
identify P-waves from an ECG signal received by the sensing module using a previously selected pair of electrodes;
control the trigger signal emitting device to transmit wireless trigger signals in response to identifying the P-waves using the previously selected pair of electrodes;
wherein comparing the P-wave amplitudes and selecting the first pair of electrodes is performed during the identifying P-waves from the previously selected ECG signal.

20. The device of claim 11, wherein identifying the P-wave comprises:
sensing a plurality of events based on threshold crossings of the first ECG signal;
sensing an R-wave from a second sensing vector;
setting a P-wave sensing window in response to the sensed R-wave;
sensing a T-wave from one of the second sensing vector and a third sensing vector;
rejecting ones of the plurality of sensed events that occur outside the P-wave sensing window; and
rejecting ones of the plurality of sensed events that occur simultaneously with the sensed R-wave or the sensed T-wave;
the first device further comprising a trigger signal controller, the first device configured to pass a P-wave sense signal to the trigger signal controller in response to a non-rejected one of the plurality of events, the trigger signal controller configured to control the trigger signal emitting device to emit the wireless trigger signal in response to acquiring the P-wave sense signal.

21. A non-transitory, computer-readable storage medium storing a set of instructions that cause an implantable medical device system including an intracardiac pacemaker to perform a method, the method comprising:
acquiring by an implantable medical device sensing module a first cardiac signal using a first pair of electrodes of a plurality of available electrode pairs that are implanted outside the cardiovascular system, the first pair of electrodes defining a sensing vector that is approximately parallel to a cranial-caudal axis of the patient;

generating a first electrocardiogram (ECG) signal based on the first cardiac signal;
identifying a P-wave from the first ECG signal;
transmitting a wireless trigger signal from an emitting device to the intracardiac pacemaker in response to identifying the P-wave; and
delivering a pacing therapy by the pacemaker in response to the trigger signal.

* * * * *